US012638909B2

(12) United States Patent
Gompertz

(10) Patent No.: US 12,638,909 B2
(45) Date of Patent: May 26, 2026

(54) OR RELATING TO EARPIECES

(71) Applicant: Nicholas Roy Gompertz, Rutland (GB)

(72) Inventor: Nicholas Roy Gompertz, Rutland (GB)

(73) Assignee: Earswitch Ltd. (GB)

( * ) Notice: Subject to any disclaimer, the term of this patent is extended or adjusted under 35 U.S.C. 154(b) by 0 days.

(21) Appl. No.: 18/015,765

(22) PCT Filed: Jul. 16, 2021

(86) PCT No.: PCT/GB2021/051829
§ 371 (c)(1),
(2) Date: Jan. 12, 2023

(87) PCT Pub. No.: WO2022/013566
PCT Pub. Date: Jan. 20, 2022

(65) Prior Publication Data
US 2023/0273673 A1 Aug. 31, 2023

(30) Foreign Application Priority Data

Jul. 16, 2020 (GB) ...................................... 2011013
Dec. 1, 2020 (GB) ...................................... 2018958
(Continued)

(51) Int. Cl.
*G06F 3/01* (2006.01)
*A61B 5/00* (2006.01)
*H04R 1/10* (2026.01)

(52) U.S. Cl.
CPC .............. *G06F 3/01* (2013.01); *A61B 5/6817* (2013.01); *H04R 1/1091* (2013.01); *G06F 3/013* (2013.01)

(58) Field of Classification Search
CPC ... G06F 3/00; G06F 3/01; G06F 3/013; G06F 3/016; G06F 3/017; G06F 3/0219;
(Continued)

(56) References Cited

U.S. PATENT DOCUMENTS

| | | | | |
|---|---|---|---|---|
| 9,928,728 B2 * | 3/2018 | Umminger, III | ....... | G08C 17/00 |
| 11,223,915 B2 * | 1/2022 | McKinney | ........... | H04R 25/604 |

(Continued)

FOREIGN PATENT DOCUMENTS

GB        2570013 A  *  7/2019  ............... A61F 4/00

OTHER PUBLICATIONS

Gruters et al., "The Eardrums Move When the Eyes Move: A Multisensory Effect on the Mechanics of Hearing", PNAS, published online Jan. 23, 2018, www.pnas.org/cgi/doi/10.1073/pnas.1717948115, 10 pages.
(Continued)

*Primary Examiner* — Franklin D Balseca
(74) *Attorney, Agent, or Firm* — Buchanan Ingersoll & Rooney PC

(57) ABSTRACT
An apparatus for detecting ear structure movements or changes, or changes in pressure in the ear-canal of a user, in order to control or affect the function of an associated device. The apparatus includes a sensor apparatus capable of being worn by the user to be located in or adjacent an ear-canal of the user. The sensor apparatus includes at least one sensor being located and configured to detect and capture sensor data relating to middle ear, ear-drum complex, ear-drum margin, and/or other ear structure movements or changes of characteristics, or changes in pressure in the ear-canal of the user. A device is provided for processing and analysing sensor data from the sensor apparatus. The device analyses sensor data concerning: eye movement or directional auditory attention or focus data, and/or voluntary control data.

21 Claims, 20 Drawing Sheets

(30)        Foreign Application Priority Data

Dec. 28, 2020    (GB) ..................................... 2020646
Jan. 10, 2021    (GB) ..................................... 2100287

(58) Field of Classification Search
    CPC ....... A61B 5/68; A61B 5/6801; A61B 5/6802;
            A61B 5/6803; A61B 5/6813; A61B
            5/6815; A61B 5/6817; H04R 1/10; H04R
            1/1091; H04R 1/1041; H04R 1/1008;
                                    H04R 1/1016
    See application file for complete search history.

(56)        References Cited

U.S. PATENT DOCUMENTS

| | | | |
|---|---|---|---|
| 11,523,229 B2 * | 12/2022 | Boley .................... | H04R 25/40 |
| 11,614,798 B2 * | 3/2023 | Muehlhausen ......... | G06F 3/013 |
| | | | 345/156 |
| 2012/0001846 A1 * | 1/2012 | Taniguchi ............... | G06F 1/163 |
| | | | 345/156 |
| 2019/0038130 A1 * | 2/2019 | Lawrence .............. | A61B 5/036 |
| 2019/0253812 A1 | 8/2019 | Gallego | |

OTHER PUBLICATIONS

International Search Report and Written Opinion for International
Application No. PCT/GB2021/051829, dated Nov. 2, 2021, 11
pages.
Zahn et al., "Multifocal Displays: Review and Prospect", Photonix,
2020, 1:10, 31 pages.

* cited by examiner

FIGURE 6

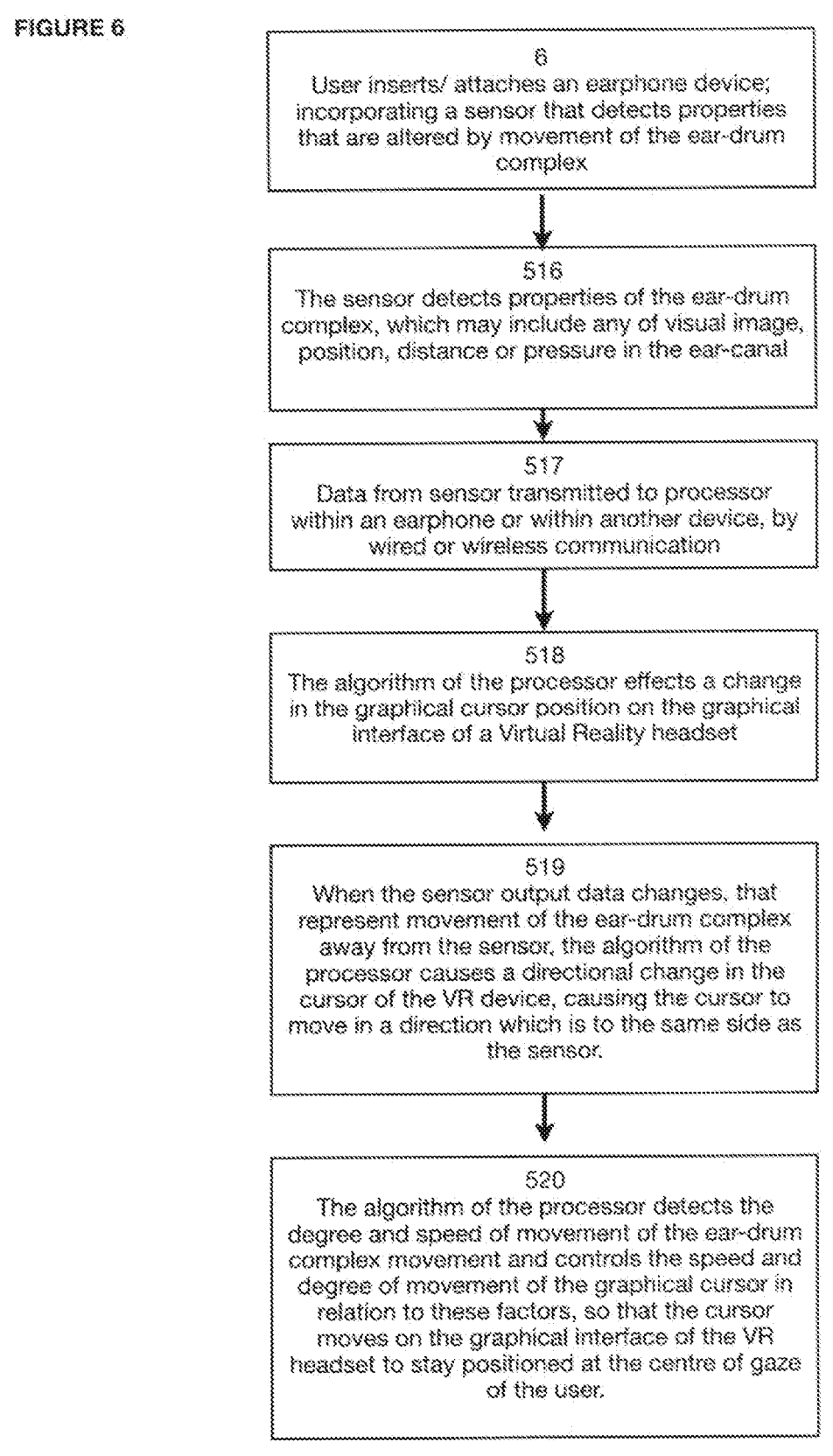

6
User inserts/ attaches an earphone device;
incorporating a sensor that detects properties
that are altered by movement of the ear-drum
complex 516
The sensor detects properties of the ear-drum
complex, which may include any of visual image,
position, distance or pressure in the ear-canal 517
Data from sensor transmitted to processor
within an earphone or within another device, by
wired or wireless communication 518
The algorithm of the processor effects a change
in the graphical cursor position on the graphical
interface of a Virtual Reality headset 519
When the sensor output data changes, that
represent movement of the ear-drum complex
away from the sensor, the algorithm of the
processor causes a directional change in the
cursor of the VR device, causing the cursor to
move in a direction which is to the same side as
the sensor.

520
The algorithm of the processor detects the
degree and speed of movement of the ear-drum
complex movement and controls the speed and
degree of movement of the graphical cursor in
relation to these factors, so that the cursor
moves on the graphical interface of the VR
headset to stay positioned at the centre of gaze
of the user.

FIGURE 7

6
User inserts/ attaches an earphone device in each ear; incorporating a sensor that detects properties that are altered by movement of the ear-drum complex.

516
The sensor detects properties of the the ear-drum complex, which may include any of visual image, position, distance or pressure in the ear-canal

521
Data from sensors is transmitted to both the processor within the earphone device, of the same ear, and the processor within the device in the opposite ear

522
The algorithm detects the difference between the data input from the sensor in each ear and this effects a change in the output of the processor to control connected user interfaces, by wired or wireless communication.

523
The algorithm of the processor detects the degree and speed of movement of the ear-drum complex movement and controls the speed and degree of movement in relation to these factors, so that the cursor moves on the graphical interface of the AR headset to stay positioned at the centre of gaze of the user.

FIGURE 8

> 6
> User inserts/ attaches a hearing aid, or assistive hearing or hearable device; incorporating a sensor that detects properties that are altered by movement of the ear-drum complex

> 516
> Sensor detects properties of the the ear drum-complex, which may include any of visual image, position, distance or pressure in the ear-canal

> 524
> Data from sensor, including data indicating amplitude/degree, and/or direction of movement is transmitted to a processor within hearing-aid or, assistive hearing or hearable device

> 525
> The algorithm of the processor effects a change in a connected interface/ device dependent on the amplitude/ degree, direction and/or speed of movement of the ear-drum complex

> 526
> The algorithm of the processor effects a change in a graphical interface "slider" control, effecting a movement of the graphical slider control and associated proportionate increase in volume of sound output from the connected device, which is in proportion to the amplitude/degree and speed of voluntary movement of the ear-drum complex.

FIGURE 11

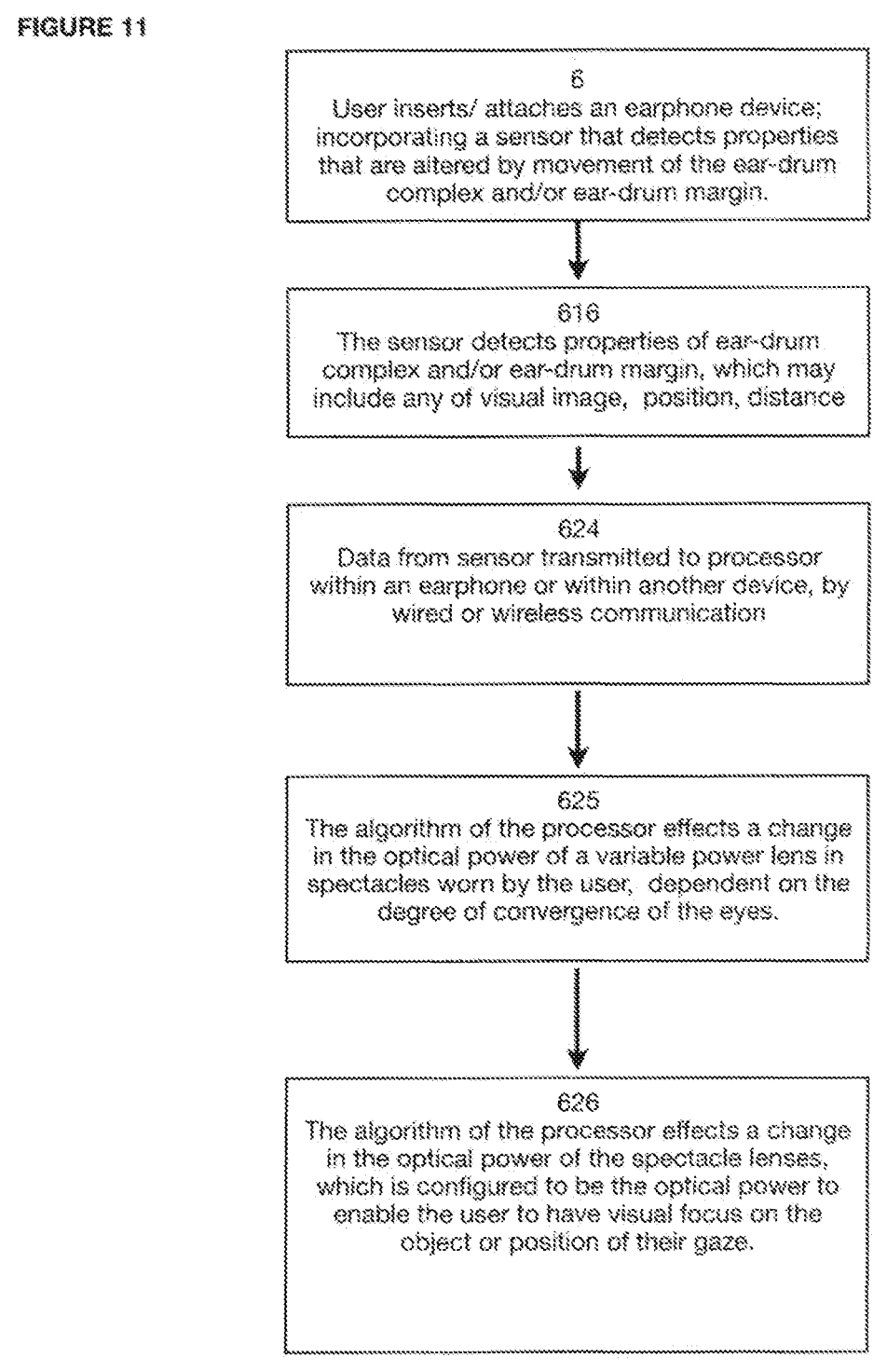

6
User inserts/ attaches an earphone device;
incorporating a sensor that detects properties
that are altered by movement of the ear-drum
complex and/or ear-drum margin.

616
The sensor detects properties of ear-drum
complex and/or ear-drum margin, which may
include any of visual image, position, distance 624
Data from sensor transmitted to processor
within an earphone or within another device, by
wired or wireless communication 625
The algorithm of the processor effects a change
in the optical power of a variable power lens in
spectacles worn by the user, dependent on the
degree of convergence of the eyes.

626
The algorithm of the processor effects a change
in the optical power of the spectacle lenses,
which is configured to be the optical power to
enable the user to have visual focus on the
object or position of their gaze.

FIGURE 12

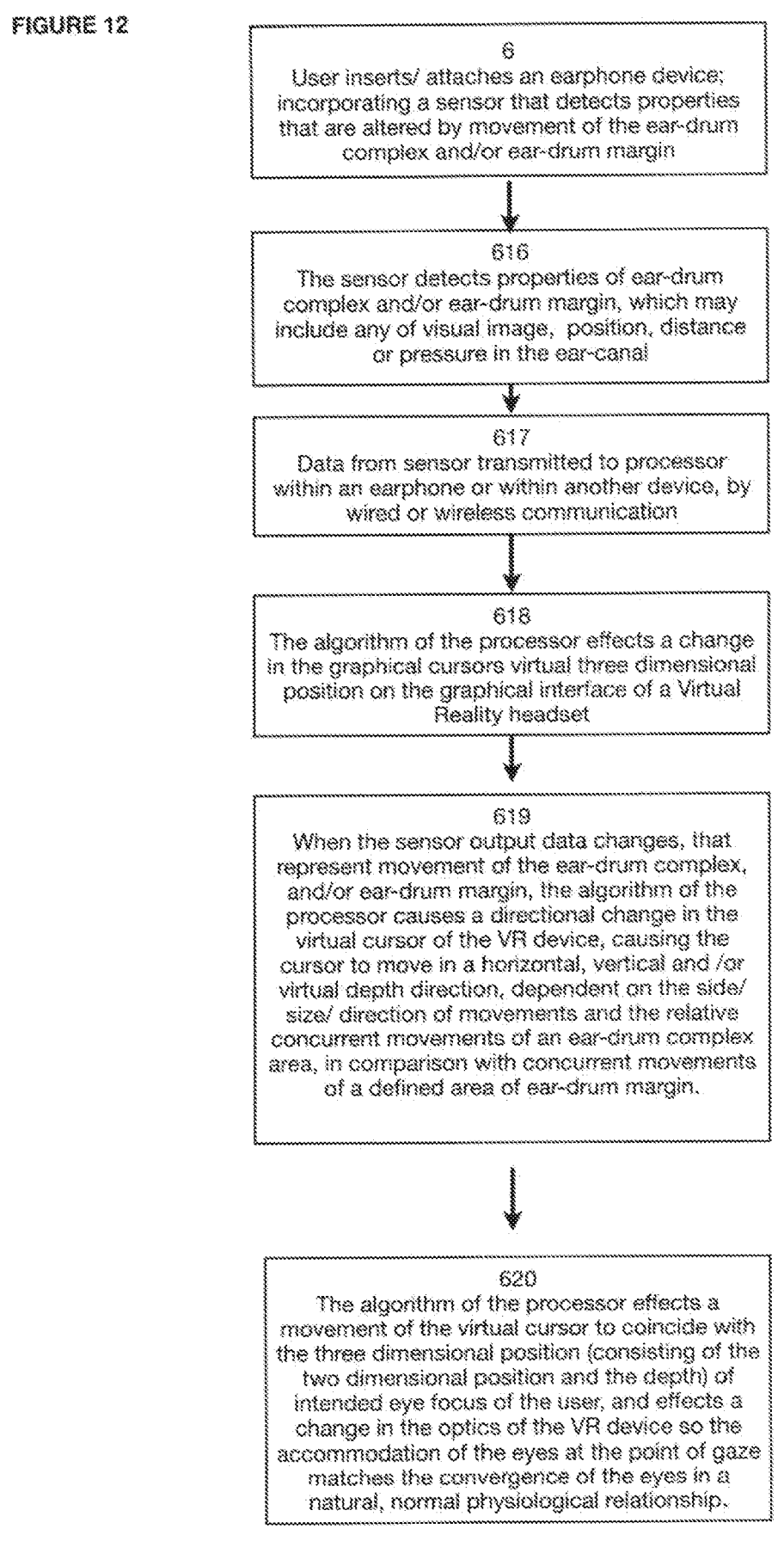

```
┌─────────────────────────────────────┐
│                 6                    │
│  User inserts/ attaches an earphone  │
│  device; incorporating a sensor that │
│  detects properties that are altered │
│  by movement of the ear-drum         │
│  complex and/or ear-drum margin      │
└─────────────────────────────────────┘
                  │
                  ▼
┌─────────────────────────────────────┐
│                616                   │
│  The sensor detects properties of    │
│  ear-drum complex and/or ear-drum    │
│  margin, which may include any of    │
│  visual image, position, distance    │
│  or pressure in the ear-canal        │
└─────────────────────────────────────┘
                  │
                  ▼
┌─────────────────────────────────────┐
│                617                   │
│  Data from sensor transmitted to     │
│  processor within an earphone or     │
│  within another device, by           │
│  wired or wireless communication     │
└─────────────────────────────────────┘
                  │
                  ▼
┌─────────────────────────────────────┐
│                618                   │
│  The algorithm of the processor      │
│  effects a change in the graphical   │
│  cursors virtual three dimensional   │
│  position on the graphical interface │
│  of a Virtual Reality headset        │
└─────────────────────────────────────┘
                  │
                  ▼
┌─────────────────────────────────────┐
│                619                   │
│  When the sensor output data         │
│  changes, that represent movement    │
│  of the ear-drum complex,            │
│  and/or ear-drum margin, the         │
│  algorithm of the processor causes   │
│  a directional change in the         │
│  virtual cursor of the VR device,    │
│  causing the cursor to move in a     │
│  horizontal, vertical and /or        │
│  virtual depth direction, dependent  │
│  on the side/ size/ direction of     │
│  movements and the relative          │
│  concurrent movements of an          │
│  ear-drum complex area, in           │
│  comparison with concurrent          │
│  movements of a defined area of      │
│  ear-drum margin.                    │
└─────────────────────────────────────┘
                  │
                  ▼
┌─────────────────────────────────────┐
│                620                   │
│  The algorithm of the processor      │
│  effects a movement of the virtual   │
│  cursor to coincide with the three   │
│  dimensional position (consisting of │
│  the two dimensional position and    │
│  the depth) of intended eye focus    │
│  of the user, and effects a change   │
│  in the optics of the VR device so   │
│  the accommodation of the eyes at    │
│  the point of gaze matches the       │
│  convergence of the eyes in a        │
│  natural, normal physiological       │
│  relationship.                       │
└─────────────────────────────────────┘
```

FIGURE 13

6
User inserts/ attaches an earphone device in
each ear; incorporating a sensor that detects
properties that are altered by movement of the
ear-drum complex, and/or ear-drum margin.

616
The sensor detects properties of ear-drum
complex and/or ear-drum margin, which may
include any of visual image,  position, distance
or pressure in the ear-canal

617
Data from sensor transmitted to processor
within an earphone or within another device, by
wired or wireless communication 622
The algorithm of the processor effects a change
in the movement and position of the robotic
hand of a prosthetic robotic upper arm.

623
The algorithm of the processor effects a
movement of the prosthetic limb to coincide
with the three dimensional position of intended
eye focus of the user, such that the robotic hand
of the prosthesis if positioned adjacent the point
or object of focus, enabling other controls to
cause the hand to grasp an object at the
position of intended eye focus.

FIGURE 16

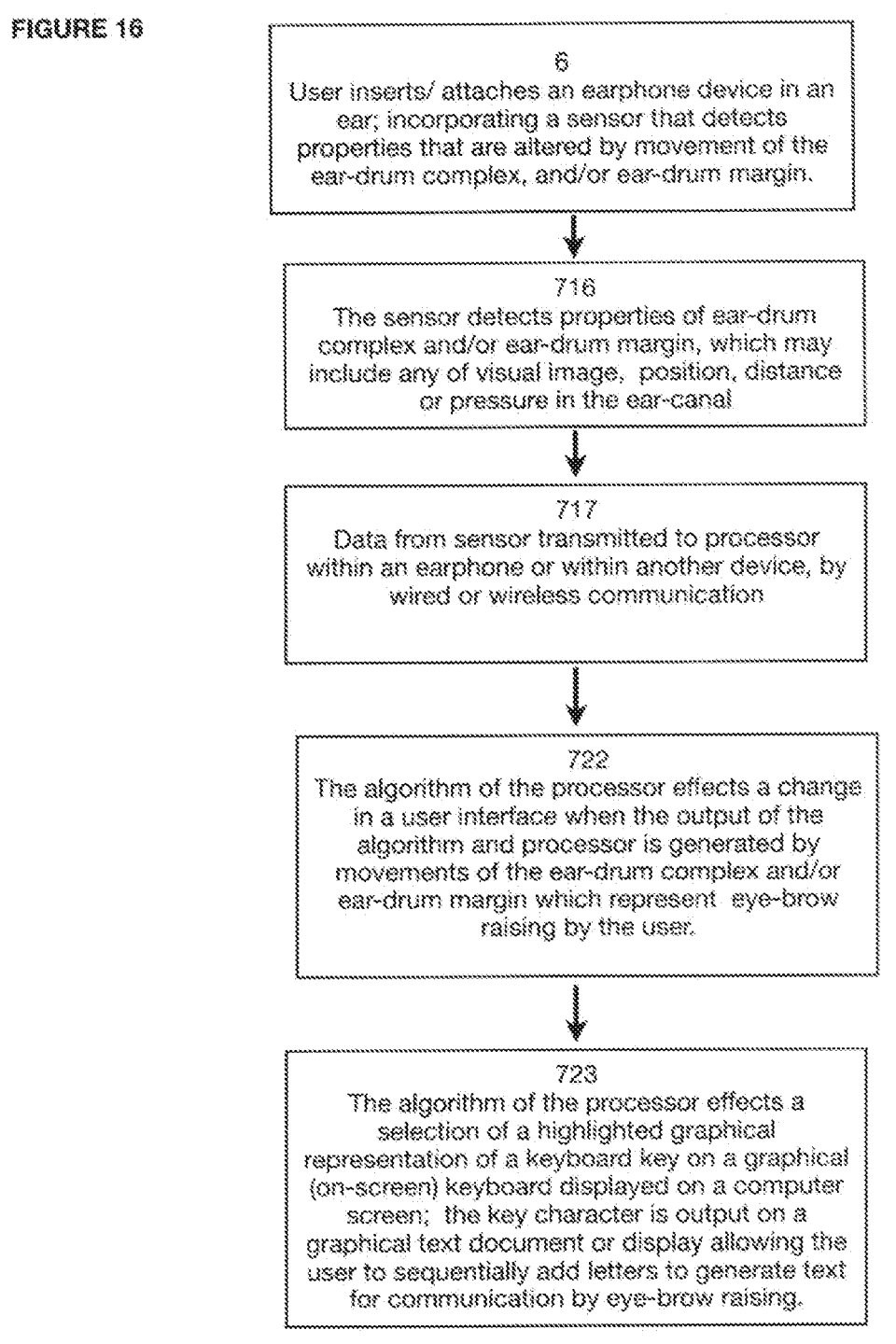

6
User inserts/ attaches an earphone device in an ear; incorporating a sensor that detects properties that are altered by movement of the ear-drum complex, and/or ear-drum margin.

716
The sensor detects properties of ear-drum complex and/or ear-drum margin, which may include any of visual image, position, distance or pressure in the ear-canal 717
Data from sensor transmitted to processor within an earphone or within another device, by wired or wireless communication 722
The algorithm of the processor effects a change in a user interface when the output of the algorithm and processor is generated by movements of the ear-drum complex and/or ear-drum margin which represent eye-brow raising by the user.

723
The algorithm of the processor effects a selection of a highlighted graphical representation of a keyboard key on a graphical (on-screen) keyboard displayed on a computer screen; the key character is output on a graphical text document or display allowing the user to sequentially add letters to generate text for communication by eye-brow raising.

FIGURE 17

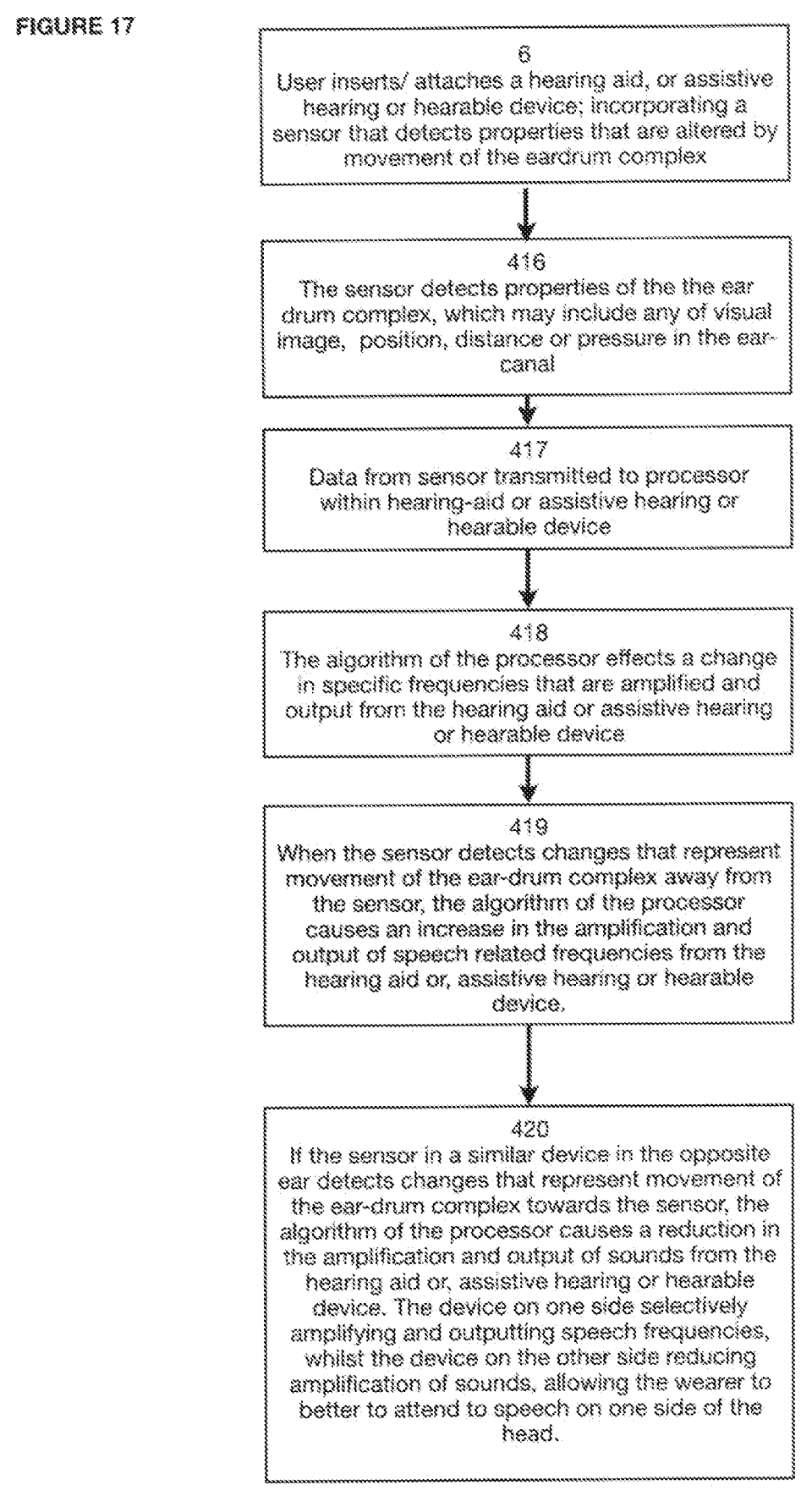

6
User inserts/ attaches a hearing aid, or assistive hearing or hearable device; incorporating a sensor that detects properties that are altered by movement of the eardrum complex

↓

416
The sensor detects properties of the the ear drum complex, which may include any of visual image, position, distance or pressure in the ear-canal

↓

417
Data from sensor transmitted to processor within hearing-aid or assistive hearing or hearable device

↓

418
The algorithm of the processor effects a change in specific frequencies that are amplified and output from the hearing aid or assistive hearing or hearable device

↓

419
When the sensor detects changes that represent movement of the ear-drum complex away from the sensor, the algorithm of the processor causes an increase in the amplification and output of speech related frequencies from the hearing aid or, assistive hearing or hearable device.

↓

420
If the sensor in a similar device in the opposite ear detects changes that represent movement of the ear-drum complex towards the sensor, the algorithm of the processor causes a reduction in the amplification and output of sounds from the hearing aid or, assistive hearing or hearable device. The device on one side selectively amplifying and outputting speech frequencies, whilst the device on the other side reducing amplification of sounds, allowing the wearer to better to attend to speech on one side of the head.

FIGURE 18

6
User inserts/ attaches a hearing aid, or assistive hearing or hearable device in each ear; each incorporating a sensor that detects properties that are altered by movement of the eardrum complex

416
Sensor detects properties of the the ear drum complex, which may include any of visual image, position, distance or pressure in the ear-canal

421
Data from sensor transmitted to both the processor within the hearing-aid, or assistive hearing or hearable device, of the same ear, and the processor within the device in the opposite ear

418
The algorithm of the processor effects a change in specific frequencies that are amplified and output, from the hearing aid or assistive hearing or hearable device

422
The algorithm detects the difference between data from the sensor in each ear and increases the amplification of output of speech related frequencies from the hearing aid or, assistive hearing or hearable device, on the side that the ear-drum moves away from the sensor.

423
The difference in reciprocal movement of each eardrum complex, results in the algorithm of the processor in each ear device, reciprocally altering the amplification and output of sounds from the hearing aid or, assistive hearing or hearable device, in each ear. The device on one side selectively amplifying and outputting speech frequencies, whilst the device on the other side reducing amplification of sounds, allowing the wearer to better to attend to speech on one side of the head.

FIGURE 19

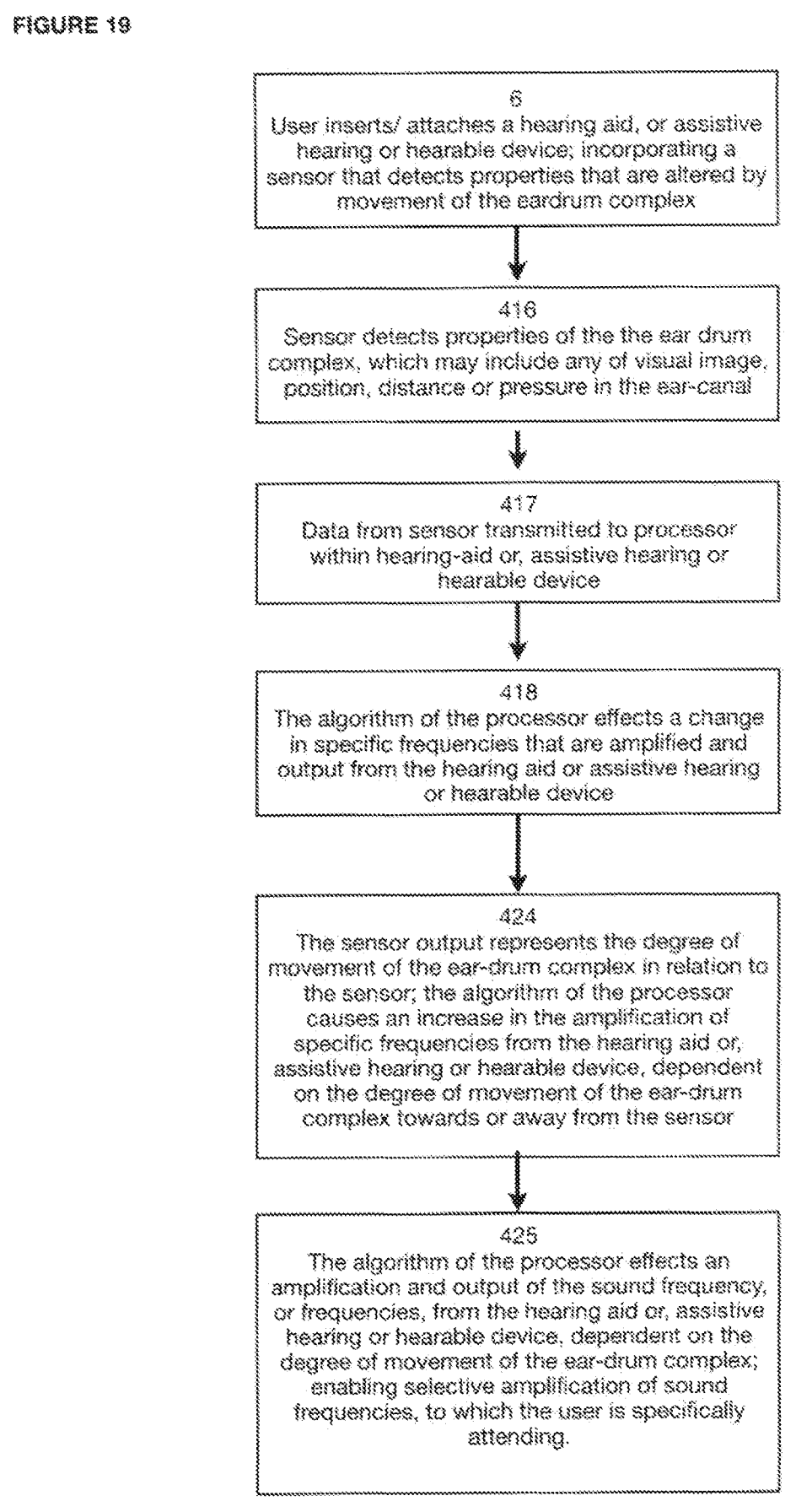

```
┌─────────────────────────────────────────┐
│                    6                     │
│  User inserts/ attaches a hearing aid, or│
│  assistive hearing or hearable device;   │
│  incorporating a sensor that detects     │
│  properties that are altered by movement │
│  of the eardrum complex                  │
└─────────────────────────────────────────┘
                    │
                    ▼
┌─────────────────────────────────────────┐
│                   416                    │
│  Sensor detects properties of the the ear│
│  drum complex, which may include any of  │
│  visual image, position, distance or     │
│  pressure in the ear-canal               │
└─────────────────────────────────────────┘
                    │
                    ▼
┌─────────────────────────────────────────┐
│                   417                    │
│  Data from sensor transmitted to processor│
│  within hearing-aid or, assistive hearing │
│  or hearable device                      │
└─────────────────────────────────────────┘
                    │
                    ▼
┌─────────────────────────────────────────┐
│                   418                    │
│  The algorithm of the processor effects a│
│  change in specific frequencies that are │
│  amplified and output from the hearing aid│
│  or assistive hearing or hearable device │
└─────────────────────────────────────────┘
                    │
                    ▼
┌─────────────────────────────────────────┐
│                   424                    │
│  The sensor output represents the degree │
│  of movement of the ear-drum complex in  │
│  relation to the sensor; the algorithm of│
│  the processor causes an increase in the │
│  amplification of specific frequencies   │
│  from the hearing aid or, assistive      │
│  hearing or hearable device, dependent   │
│  on the degree of movement of the ear-drum│
│  complex towards or away from the sensor │
└─────────────────────────────────────────┘
                    │
                    ▼
┌─────────────────────────────────────────┐
│                   425                    │
│  The algorithm of the processor effects an│
│  amplification and output of the sound   │
│  frequency, or frequencies, from the     │
│  hearing aid or, assistive hearing or    │
│  hearable device, dependent on the       │
│  degree of movement of the ear-drum      │
│  complex; enabling selective amplification│
│  of sound frequencies, to which the user │
│  is specifically attending.              │
└─────────────────────────────────────────┘
```

Figure 20

6
User inserts/ attaches a hearing aid, or assistive hearing or hearable device or other earphone device; incorporating a sensor that detects properties that are altered by movement of the eardrum complex

↓

416
Sensor detects properties of the the ear drum complex, which may include any of visual image, position, distance or pressure in the ear-canal

↓

426
The hearing-aid or, assistive hearing or hearable device or other earphone device emits a "test sound"

↓

416
Sensor detects properties of the the ear drum complex, which may include any of visual image, position, distance or pressure in the ear-canal

↓

417
Data from sensor transmitted to processor within hearing-aid or, assistive hearing or hearable device or other earphone device

↓

427
The algorithm of the processor effects a change in the device dependent on the movement/ vibration or resonance of the ear-drum complex in response to one or more "test sounds"

↓

428
The algorithm of the processor programs a change in the profile of the degree to which specific frequencies of sound are amplified and/ or transmitted by the device subsequently; enabling improved hearing of frequencies to which the ear-drum demonstrates lower than a predefined movement/ vibration or resonance in response to a similar frequency "test sound"

OR RELATING TO EARPIECES

CROSS REFERENCE TO RELATED APPLICATIONS

This application is a U.S. National Phase Patent Application filed under 35 U.S.C. § 371 claiming benefit to International Patent Application No. PCT/GB2021/051829, filed Jul. 16, 2021, which claims priority to GB Patent Application No. 2011013.6, filed Jul. 16, 2020, GB Patent Application No. 2018958.5, filed Dec. 1, 2020, GB Patent Application No. 2020646.2, filed Dec. 28, 2020, and GB Patent Application No. 2100287.8, filed Jan. 10, 2021, the contents of these applications being incorporated by reference in their entirety.

FIELD OF THE INVENTION

The present invention relates to improvements in an earpiece, earphone, hearing-aid or other in-ear device. In particular, the invention relates to an apparatus an associated method for detecting ear structure movements or changes, or changes in pressure in the ear-canal of a user in order to control or affect the function of an associated device.

BACKGROUND OF THE INVENTION

A well-established difficulty for users of augmented and virtual reality devices (AR and VR respectively) and other head-mounted and heads-up displays and interfaces is how a user interfaces with the device and any graphical interface. Interfaces have been developed with hand-held controllers, head tracking, voice commands and hand tracking, but a simple interface that is hands-free, silent and invisible, and does not interrupt a user's activities has not been identified previously. Eye-tracking has proven problematic in view of the difficult triangulation of the eyes from devices that are mounted so close to the face or in-front of a field of view. Other user interfaces may also benefit from being hands-free, invisible and provide silent control of directionality, for example, in steering mechanical devices—including electric wheelchairs for people with significant loss of muscle control (such as motor neurone disease/amyotrophic lateral sclerosis)—or recreational or industrial devices or uses, but none presently exist in the art.

The present invention is directed to an apparatus and associated method for providing directional and/or variable or dynamic or graduated control for electronic devices and interfaces without the disadvantages associated with the prior art.

A well-established problem with ageing is presbyopia (the increasing difficulty to focus on near objects owing to age related eye lens changes). This is often corrected by use of reading spectacles, or spectacles with differing lens powers within different areas of the lens. This is limited by the need to wear and remove the spectacles according to activity with monofocal lenses, and adjusting the head position with bifocal or progressive lens spectacles. Monovision spectacles with a lens for near vision in one lens and far vision in the other are only tolerated by a small proportion of users.

A well-established difficulty for users of augmented reality (AR) and virtual reality (VR) devices, head-mounted displays, other near-eye displays, and heads-up displays and similar interfaces, is how the user interfaces and provides input to the device and any graphical interface. Interfaces have been developed with hand-held controllers, head tracking, voice commands and hand tracking, but a simple interface that is hands-free, silent and invisible and does not interrupt the users activities has not been identified previously. Eye-tracking has proven problematic in view of the difficult triangulation of the eyes from devices that are mounted close to the face or in-front of a field of view. Some methods claim to improve eye-tracking interface performance and reduce power consumption by anticipating approximate horizontal movement of the eyes by detecting reciprocal pressure changes in ear-canals related to horizontal eye-movement. However, these methods cannot provide a measure of convergence and central eye movement.

A further established difficulty with AR and VR devices, and other near-eye displays, is the conflicting information that a user's brain receives because the convergence of the eyes does not match the visual focus (accommodation) of the eyes on the display. This is termed the vergence-accommodation conflict (Reference: Multifocal displays: review and prospect; Zhan et al. Photonix (2020) 1:10 https://doi.org/10.1186/s43074-020-00010-0:30 Mar. 2020). The eyes converge to 3D objects presented at different perceived distances at the correct angles for the distance perceived. However, the eyes focus (accommodate) at a fixed distance determined by the physical display and viewing optics. The brain therefore receives conflicting information as the vergence angles of the two eyes' fixation is aligned with the perceived distance of the image but the focus (accommodation) is aligned with an image being viewed at a different distance. This conflict is reported to limit the depth perception in these displays and cause visual fatigue, which may affect the ability to tolerate prolonged use of these displays and cause symptoms after viewing also, including eye strain, visual blurring and headache.

Methods for reducing or preventing the vergence-accommodation conflict include using multifocal displays which are controlled to enable the user to accommodate to focus on the display at a virtual depth that coincides with the detected vergence angle. This correctly fuses the information on vergence and accommodation that is delivered to the user's brain, enabling more natural vision depth and three dimensional perception. Multifocal displays may be provided by methods including continuously tunable lens, tunable reflectors and switchable lenses. These displays have been developed using eye trackers detecting movement of both eyes, by camera sensors directed at the eyes of the user to locate the direction of gaze; and alters the focal length of the display depth to match the vergence angle detected by the eye-tracker cameras. These may use focus-tunable optics; lenses that change their focal power in real time, or a motor that mechanically adjusts the distance between screen and magnifying lenses in real time. These methods are limited by the need for eye-tracking sensors located in these wearable devices. These eye-tracking sensor/imagers are limited in their ability to track the convergence angle of the eyes due to the limitation of the distance from the eyes; the angle needed to triangulate the eye movement needs the sensors to be sufficiently distanced from the eyes. This method also does not provide an accurate measure of vertical eye movement.

The "cocktail party" dilemma refers to the problem that hearing-aids may amplify general ambient sounds in addition to the voice or sound of particular interest to the user, making it difficult to hear voices or other sounds of interest to the user when there is background noise. Some known methods propose driving directional control of hearing aids by detecting electronic impulses (EMG signals) in external ear muscles that, in other mammals, are associated with external ear (pinna) movements. The EMG activity of these muscles is also detectable during auditory attention in humans; however, this method is hampered by the need for reliable electrical contacts, and the EMG interference from other larger, head and facial muscles.

Other prior art aims to improve eye-tracking interface performance and reduce power consumption by anticipating approximate horizontal movement of the eyes, by detecting reciprocal pressure changes in ear-canals related to horizontal eye-movement. However, pressure measurements rely on a sealed auditory canal, and are affected by jaw movements, such as talking and chewing. This only provides horizontal detection of eye movement and cannot therefore detect the two dimensional position of centre of eye-gaze, and so this does not provide a replacement for current eye tracking technology which relies on eye-imagers or cameras.

The invention is directed to an apparatus and method for detecting eye-movements, intended eye focal depth, and directional auditory focus without the disadvantages associated with the prior art.

Some people with motor disabilities (disabilities that prevent normal control of muscular function) cannot communicate normally as they are unable to generate speech. People with severe disabilities may be able to use existing assistive technologies using switches that are triggered by movements that they are still able to control, such as cheek movements, eye movements (such as by eye tracking) or head movement. Further, simple switch technology has been used to allow people with communication difficulties—owing to motor problems (difficulty controlling muscle movement), such as cerebral palsy, multiple sclerosis, motor neurone disease or with neck trauma—to interface with communication aids and other user interfaces, and such interfaces are known to control electronic devices such as electronic wheelchairs, computers and other user interface outputs to assist with communication, mobility, activities of daily living and entertainment (assistive technologies) and other functions. Communication aids may allow a user to select a letter or word on a graphical user interface by simple switch activation during scanning of an on screen keyboard display, or activate a function by selecting an icon, as well as other output options. However, people with the most severe disabilities may find it difficult to control the movements that are currently detectable and used to trigger assistive technology. This may be because of absence of control of the muscles because of abnormal involuntary uncontrollable movements which interfere with detection of more subtle voluntary movements. An example of this is if a person has athetoid involuntary movements which causes unpredictable involuntary head movements that interfere with eye tracking technology or the ability of a purposeful head movement to trigger a switch.

Other known methods of assistive technology control include detecting specific movement of the ear-drum complex caused by voluntary movement of the tensor tympani muscle by sensors in earphones or earpieces. However, this is limited in its application because a proportion of the population are either not aware of this movement and/or are not able to voluntarily control the tensor tympani muscle.

Current established interfaces include touch, voice and eye tracking; however all have limitations including: interrupting a user's activities; not being hands-free; requiring sensors that are positioned or worn in front of the eyes; not having a suitable "click to select" interface (for eye tracking/virtual reality (VR)/augmented reality (AR) and other similar interfaces). Current technology may control user interfaces with such methods as touch sensitive screens or displays, physical buttons, and voice sensitive commands and accelerometers; however, these methods are all either visible or audible, making control of these technologies obvious to people other than the user.

The present invention is directed to a method and apparatus for detecting facial movements, for example eye-lid closure and/or eye-brow raising, to enable control of interfaces or associated devices without the disadvantages of the prior art.

A well-established difficulty for users of hearing-aids/hearing-assistive devices is that the user has difficulty distinguishing a voice or sound of interest in the presence of other back-ground noise. This has been termed the cocktail party scenario. A hearing aid or other hearing assistive device may amplify some or all of the background noise in addition to the voice or sound of interest. This can make it difficult for a user to attend to, and decode or understand the voice or sound of interest. The term for preferentially attending to a preferred sound or voice is 'selective auditory attention'. This problem is common to known smart earphones (subsequently called hearables) which are marketed as having assistive hearing functions to improve transmission and amplifying sounds of specific interest to a wearer, but which often simply amplify the wrong noises.

It is known to attempt to provide control of hearing aids by detecting electroencephalogram (EEG) signals to detect the frequencies of sound of interest so that a hearing aid or assistive device may be controlled to selectively amplify these frequencies. These methods have limitations in method and user acceptability, and EEG monitoring requires a well applied and electrically connected electrode to the skin, usually requiring electrode gel or pads on the scalp to obtain measurements which can be affected by muscle artefact. In the above, one electrode is within the hearing aid itself but, again, has the limitations of requiring a reliable contact and requiring a second reference electrode on the scalp.

User acceptability of hearing aids and hearing assistive devices may be limited by the inability to provide selective auditory attention at a level that a user would expect from their pre-morbid healthy hearing status.

The current invention is directed to an apparatus and method for providing selective auditory attention without the disadvantages associated with the prior art.

SUMMARY OF THE INVENTION

According to a first aspect, the present invention provides an apparatus for detecting ear structure movements or changes, or changes in pressure in the ear-canal of a user, in order to control or affect the function of an associated device, the apparatus comprises:

sensor means capable of being worn by said user to be located in or adjacent an ear-canal of the said user and at least one sensor being located and configured to detect and capture sensor data relating to middle ear, ear-drum complex, ear-drum margin, and/or other ear structure movements or changes of characteristics, or changes in pressure in the ear-canal of said user; and means for processing and analysing sensor data from the sensor means, wherein the means for processing and analysing data analyses sensor data concerning one or more of the group comprising:

eye movement or directional auditory attention or focus data, by analysing data relating to a degree, speed, size of movement or change, or duration of movement of the middle-ear, ear-drum complex, ear-drum margin, and/or associated ear structures, or changes of pressure in the ear-canal;

voluntary control data, by analysing data relating to a degree, speed, size of movement or change, or duration of movement of the middle-ear, ear-drum complex, ear-drum margin, and/or associated ear structures, or changes of pressure in the ear-canal;

gaze focusing movement data, by analysing data relating to two-dimensional eye-movement and eye-convergence and central gaze;

facial, head and/or neck movement data, by analysing data relating to ear structure movements or changes, or changes in pressure in the ear-canal, associated with facial, head and/or neck movement;

intended selective auditory attention data, by analysing data relating to ear structure movements or changes, or changes in pressure in the ear-canal of a user; and/or sound response data, by analysing data relating to ear structure movements or changes, or changes in pressure in the ear-canal of a user in response to sound, such that, through identification of change(s) or difference(s) in the sensor data, the apparatus is capable of controlling or affecting the function of an associated device.

Preferably, the ear-drum complex is the ear-drum, the malleus, or both the ear-drum and malleus. Preferably, the ear-drum may move with or without it being in response to sound. Preferably, the apparatus is provided in an earpiece, earphone, hearing-aid, assistive hearing or other in-ear device.

Preferably, the sensor means is configured to detect change in any one or more of the group comprising:

movement of the eardrum complex, or associated ear structures, through two or three dimensional analysis or image processing;

distance from the sensor means;

direction of movement, size of movement, degree of movement, duration of movement, position, and/or shape of a part or whole of the ear-drum complex, auditory canal, ear-drum margin, adjacent wall of auditory tube (ear-canal) and/or associated or other ear structure(s);

pressure in the ear-canal;

colour of at least part of the ear-drum complex or related ear structures;

frequency of vibration of at least part of the ear-drum complex;

reflection;

any other measure indicating movement of the ear-drum complex and/or associated structures; and/or any one or more of the above providing a discernible difference between different areas of the same ear structure or different ear structures, or a pair of sensors, each associated with a different ear of the user.

Preferably, the sensor means comprises any one or more of the group comprising:

an imaging detector, preferably a video camera or infrared video camera, with or without light source, or any other light spectrum detector, or digital holography detector;

thermal imaging detector;

a static or scanning laser detector, preferably laser Doppler vibrometry, optical coherence tomography and/or laser triangulation;

a time of flight detector;

LIDAR (laser imaging, detection, and ranging);

a photoplethysmograph (PPG) sensor, with or without oxygen saturation sensor;

a pressure detector;

a sound detector, preferably a microphone, optionally including a remote microphone;

an ultrasonic detector, preferably including a polyvinylidene fluoride film (PVDF) transducer or capacitive micromachined ultrasonic transducer (CMUT); and/or any other proximity or movement detector.

Preferably, the sensor means detects changes of the ear-drum margin and/or ear-drum complex and/or other ear structures. Such changes include the distance from the sensor, position, movement, shape or colour, of the ear-drum complex and/or ear-drum margin and/or other ear structure, or change in pressure within the ear-canal. Preferably, these sensor means/detectors or any combination of sensors means/detectors detect movement of the ear-drum and/or ear-drum margin, or any aspect of ear-drum complex or ear drum margin or other ear structures, or any change in characteristic including a change in colour, or ear-canal pressure, and the data is transmitted to a processor or processors of the apparatus. Such movements may be detected relative to the position of the sensor means/detector, as applicable. Preferably, the sensor means comprises additional sensors for: detecting changes which occur during normal hearing; detecting movement of the ear-drum complex to detect pressure in the ear-canal; and/or detecting one or more biometric properties. Preferably, the sensor means detects one or more biometric properties of the user from the group comprising: oxygen saturation; blood flow; pulse rate and rhythm; respiratory rate; temperature; eustachian tube function; changes in colour or visible structural changes; and/or pathology.

Preferably, controlling or affecting the function of an associated device comprises one or more of the group comprising:

operating as an intentional switch trigger;

graduated or variable intentional control;

two or more dimensional or variable control of user interfaces;

controlling direction, amplitude and frequency of sound output of earphone device;

optical focus control;

multi-functional control of the same interface or different interfaces; change in state of a device;

control of a digital, electronic of other device, or electronic interface, including those remote from said user;

virtual or real movement control; and/or monitoring of ear-drum complex, ear-drum margin or other ear structure movements as a biometric measure of health, disease, physiological and behavioural activity.

Preferably, processing and analysing sensor data concerning eye movement or directional auditory attention or focus data provides: graduated, dynamic or variable control of interfaces by detecting movements of the middle ear; and/or intentional graduated, dynamic or variable control of interfaces by detecting (voluntary or non-voluntary) movements of the middle ear (including the ear-drum complex, being the ear-drum and malleus).

Preferably, processing and analysing sensor data concerning eye movement or directional auditory attention or focus data provides hands-free, silent, directional, variable, dynamic and/or graduated control of electronic interfaces and/or devices by movements of the middle ear. Preferably, the apparatus generates an output to control a wired or wirelessly connected interface. Preferably, the output controls movement or change in the connected interface to include, but not limited to, variable control of the degree and directionality of the device interface in response to characteristics of movements of the ear-drum complex.

Preferably, the apparatus comprises a further sensor means capable of being worn by said user to be located in or adjacent a second ear-canal of the said user to provide additional sensor data.

Preferably, the means for processing and analysing sensor data from the sensor means is capable of receiving sensor data from sensors worn in both ears of said user and is capable of utilising identified change(s) or difference(s) in the two sets of sensor data to control or affect the function of an associated device.

Preferably, the interface is controlled by an input from a single sensor or from a sensor worn in each ear of a user. Preferably, the output of the apparatus controls position or movement of a graphical interface, such as a graphical cursor, a degree of a control like a volume slider, or a direction or movement of a device, such as a wheelchair, other vehicle or robotic arm. Further preferably, the output of the apparatus controls virtual movement within a graphical menu or in a virtual or augmented reality scene or rendered graphical interface.

Preferably, the means for processing and analysing data analyses sensor data concerning ear-drum complex movement, and ear-drum margin and/or other ear structure movements in addition to ear-drum complex movement, so as to provide improved and more reliable control of the interface or associated device.

Preferably, the sensor means is configured to detect eye-convergence, gaze focusing, depth of intended visual focus, horizontal and/or vertical eye movements, or any combination thereof. Preferably, by detecting gaze focusing or eye-convergence movements of the ear, this enables central control of virtual cursors and virtual object selection, and also three-dimensional control and/or multifunctional control and change in such interfaces. Further preferably, this enables hands-free, silent three-dimensional and directional control related to two dimensional eye-movements in addition to eye-convergence, and/or directional auditory attention. Preferably, in so doing, the sensor means detects central movement of eyes, or detects an intended focus of the user (focal depth, and/or accommodation), which is associated with bilateral medial movement of the eyes towards a central focal point (convergence). The present invention includes a method and apparatus for detecting eye convergence from earphone device sensors, providing at least one extra dimension of control and, preferably, providing three-dimensional control of interfaces. Further, the invention provides three-dimensional and/or multi-functional control of any virtual or physical interface, tool, mobility device, vehicle, or any other interface, which may be near to or remote from the user. The sensor means provide a more reliable reflection of any three-dimensional change in auditory, visual focus or movement than known techniques detecting eye tracking or ear-movement. The present invention detects movements within the ear, which movement is associated with eye-movement in two dimensions and depth of intended visual focus or eye-convergence, and/or direction of auditory focus. The invention does not rely upon eye imagers per se. Without wishing to be bound by theory, during convergent eye-movements (for example when a user focuses on an object near to the face, such as during reading), a section of the ear-drum complex margin moves in association with the movement of areas of the ear-drum, including in association with movement of an area near the end of the malleus. This movement is of different character to movements of these structures related to voluntary tensor tympani control or horizontal eye movements (where, for example, the area of ear-drum near the end of the malleus may move backwards, independent of ear-drum margin movement), or vertical eye movement (where, for example, an area of the ear-drum near to the end of the malleus moves upwards, independent of movement of the ear-drum margin). Movement of the ear-drum margin is considered to have causes to include: movement of the cartilage of the ear canal by action of the external ear muscles (the *auricularis* anterior, *auricularis* posterior, *auricularis* superior), and the muscles of the pinna (the *helicis* major, *helicis* minor, transversus *auriculae, obliquus auriculae*, tragicus and antitragicus). Preferably, the invention provides control for assistive transport devices for those people whose disabilities hamper control owing to loss or reduction of muscle function; it provides graded or variable, and three-dimensional control of robotic prostheses, and, for other uses, it provides hands-free control enabling concurrent use of other devices or tools or hand activities, whilst controlling the interface silently. Further advantages include perceived improved function of VR (virtual reality)/AR (augmented reality) and other graphical, and near-eye interface devices, and their control by user intention, by incorporating an alternative to normal eye-tracking, which is detected by sensors in earphone devices. Further, by detecting central focus and near-vision focus, one can control other interfaces in a three-dimensional manner, correcting presbyopia in spectacles and other devices, and providing widely applicable assistive and augmentative communication interfaces for users with severe motor impairments.

Preferably, the sensor means is configured to detect eye-lid closure, eyebrow raising, and/or opening eyes wide, or combinations thereof.

Preferably, the sensor mean is configured to detect separate eye-lid closure, independent eyebrow raising, and/or opening of one or both eyes wide, or combinations thereof.

Preferably, the sensor means is configured to detect head and neck muscle movements Preferably, the detected ear-drum complex/margin or other ear structure movement occurs as a result of or in conjunction with facial, head and/or neck movements owing to attachment of the muscles effecting the facial, head and/or neck movements directly affecting those ear structures. Various combinations and types of movement of different areas of the ear-drum complex, ear-drum margin and/or other ear structures are associated with specific activities or movements. Further preferably, the present invention provides detection of movement related to eye-brow lifting without vertical eye-movements, which is previously unknown in the art, and eye-closure or eye-opening as a tool for controlling interfaces. The present invention provides user control of interfaces and/or associated devices in a silent, hands-free manner that does not interrupt the users' activities, or their visual focus, and provides more widespread control for a larger proportion of users without the need for intensive training. Further, it provides dual or multimodal control in various circumstances, e.g. closing each eyelid separately or raising an eyebrow independently.

Preferably, the means for controlling and/or adjusting is configured to amplify frequencies and sounds of interest.

Preferably, the apparatus provides graduated, dynamic or variable control of interfaces by detecting movements of the ear-drum complex. The present invention provides improved function of hearing aids, assistive hearing and hearable devices by controlling amplification parameters (including amplifying the frequencies and sounds of interest) through detecting the ear-drum complex changes that are associated with intended selective auditory attention.

Preferably, the apparatus comprises means for controlling and/or adjusting amplification parameters depending upon a detected response of an ear-drum to sound.

Preferably, wherein the means for controlling and/or adjusting, in use, affects and/or controls programming of the associated device to improve sound output.

Detecting a response to sound enables a more objective assessment and also adjustment of hearing function by detecting a response of the ear-drum to sounds and enabling programming of improved sound output in the earphone device, etc.

Preferably, the algorithm is capable of differentiating between different types of movement, for example by comparing different parts or regions of the same ear structure and/or by comparing different parts of different ear structures to provide several modalities of control. Most preferably, the algorithm compares at least a part of the ear-drum complex and at least a part of the ear-drum margin.

Preferably, the apparatus further comprises means for providing feedback. Most preferably, the feedback is haptic feedback provided to at least a part of the ear structure.

It is observed that vertical eye movements per se causes different movements of the ear. For example, vertical eye movement causes an area of the ear-drum near to the end of the malleus to move upwards, but this is independent from movement of the ear-drum margin—allowing one to differentiate this action from those movements intended to be detected.

According to a second aspect, the invention provides a method for detecting ear structure movements or changes, or changes in pressure in the ear-canal of a user, in order to control or affect the function of an associated device, the method comprises:

detecting and capturing sensor data from sensor means worn by the user located in or adjacent an ear-canal of the user, at least one sensor being located and configured to detect and capture sensor data relating to middle ear, ear-drum complex, ear-drum margin, and/or other ear structure movements or changes of characteristics, or changes in pressure in the ear-canal of said user; and processing and analysing sensor data concerning one or more of the group comprising:

eye movement or directional auditory attention or focus data, by analysing data relating to a degree, speed, size of movement or change, or duration of movement of the middle-ear, ear-drum complex, ear-drum margin, and/or associated ear structures, or changes of pressure in the ear-canal;

voluntary control data, by analysing data relating to a degree, speed, size of movement or change, or duration of movement of the middle-ear, ear-drum complex, ear-drum margin, and/or associated ear structures, or changes of pressure in the ear-canal;

gaze focusing movement data, by analysing data relating to two-dimensional eye-movement and eye-convergence and central gaze;

facial, head and/or neck movement data, by analysing data relating to ear structure movements or changes, or changes in pressure in the ear-canal, associated with facial, head and/or neck movement;

intended selective auditory attention data, by analysing data relating to ear structure movements or changes, or changes in pressure in the ear-canal of a user; and/or sound response data, by analysing data relating to ear structure movements or changes, or changes in pressure in the ear-canal of a user in response to sound, utilising identified change(s) or difference(s) in the sensor data to control or affect the function of an associated device.

Preferably, processing and analysing sensor data comprises detecting change in any one or more of the group comprising:

movement of the eardrum complex, or associated ear structures, through two or three dimensional analysis or image processing;

distance from the sensor means;

direction of movement, size of movement, degree of movement, duration of movement, position, and/or shape of a part or whole of the ear-drum complex, auditory canal, ear-drum margin, adjacent wall of auditory tube (ear-canal) and/or associated or other ear structure(s);

pressure in the ear-canal;

colour of at least part of the ear-drum complex or related ear structures;

frequency of vibration of at least part of the ear-drum complex;

reflection;

any other measure indicating movement of the ear-drum complex and/or associated structures;

and/or any one or more of the above providing a discernible difference between different areas of the same ear structure or different ear structures, or a pair of sensors, each associated with a different ear of the user.

Preferably, comprising controlling or affecting the function of an associated device comprises one or more of the group comprising:

operating as an intentional switch trigger;

graduated or variable intentional control;

two or more dimensional or variable control of user interfaces;

controlling direction, amplitude and frequency of sound output of earphone device;

optical focus control;

multi-functional control of the same interface or different interfaces;

change in state of a device;

control of a digital, electronic of other device, or electronic interface, including those remote from said user;

virtual or real movement control; and/or monitoring of ear-drum complex, ear-drum margin or other ear structure movements as a biometric measure of health, disease, physiological and behavioural activity.

Preferably, the method comprising processing and analysing sensor data concerning eye movement or directional auditory attention/focus data to provide: graduated, dynamic or variable control of interfaces by detecting movements of the ear-drum complex, ear-drum margin and/or other ear structure; OR intentional graduated, dynamic or variable control of interfaces by detecting voluntary movements of the ear-drum complex, ear-drum margin and/or other ear structure.

Preferably, the method comprising receiving sensor data from sensors worn in both ears of said user and utilising identified change(s) or difference(s) in the two sets of sensor data to control or affect the function of an associated device.

Preferably, the method comprising processing and analysing sensor data concerning ear-drum complex movement, and ear-drum margin and/or other ear structure movements in addition to ear-drum complex movement, to provide improved and more reliable control of the interface or associated device.

Preferably, the method comprising detecting eye-convergence, gaze focusing, depth of intended visual focus, horizontal and/or vertical eye movements, or any combination thereof.

Preferably, the method comprising detecting eye-lid closure, eyebrow raising, and/or opening eyes wide, or combinations thereof.

Preferably, the method comprising detecting separate eye-lid closure, independent eyebrow raising, and/or opening of one or both eyes wide, or combinations thereof.

Preferably, the method comprising detecting head and neck muscle movement through associated ear structure movement.

Preferably, the method comprising controlling and/or adjusting amplification parameters depending upon a detected response of an ear-drum to sound.

Preferably comprising controlling and/or adjusting amplifies frequencies and sounds of interest.

Preferably, the method comprising controlling and/or adjusting to affect and/or control programming of the associated device to improve sound output.

Preferably, the method operates on an apparatus according to the first aspect.

It has been shown that the ear-drums move reciprocally in response to planned eye-gaze movements; pressure changes have been measured during pursuit gaze showing that approximately 10 ms before a planned eye movement the pressure is reduced in the ear-canal on the side that the gaze is moving towards. In the opposite ear canal the pressure increases. This shows that the ear-drum on the same side (ipsilateral) of gaze direction is pulled inwards; a movement which is actioned by contraction of the middle ear muscle; the tensor tympani. On the opposite side (contralateral) to the gaze direction the ear-drum moves outward, owing to relaxation of the tensor tympani ("The eardrums move when the eyes move". Kurtis G. Gruters, David L. K. Murphy, Cole D. Jenson, David W. Smith, Christopher A. Shera, Jennifer M. Groh. Proceedings of the National Academy of Sciences February 2018, 115 (6) E1309-E1318).

The tensor tympani is a muscle attached to the middle ear bone or ossicle, called the malleus; which itself is attached to the inner surface of the ear-drum. This combination of the ear-drum and malleus will herein be referred to as the ear-drum complex. Contraction of the tensor tympani therefore tenses the ear-drum, and is postulated to tune the ear-drum to certain frequencies. Studies have also shown that voluntary contraction of the tensor tympani reduces transmission of lower frequency sounds, and increases the transmission of higher frequency sounds. Voluntary contraction of the tensor tympani can be seen with video imaging devices to cause the malleus to move backwards as the bone is pulled backwards and inwards.

The study "The eardrums move when the eyes move" by Kurtis G. Gruters et al, mentioned above, by showing reciprocal pressure changes within the ear-canal, indicates that the tensor tympani is a muscle of selective auditory attention. Subtle contraction of the tensor tympani occur in the ear of the side of auditory attention, so that the individual focuses their attention preferentially on that side by preferentially enabling transmission of the frequencies of interest in the ipsilateral ear.

Detecting subtle movements of the ear-drum owing to tensor tympani contraction will allow detection of the direction of eye movements. It may also detect direction of intended auditory attention when an individual "attends" to listen for sounds on one side of their head, without moving their eyes. Detecting this movement may therefore be used to detect purposeful control of an interface such as a cursor on a graphical, AR, or VR interface, by detecting either direction of eye movement, or direction of auditory attention. A user may therefore control a graphical cursor or other interface with eye movements (similarly to eye tracking), or a skilled user may control this movement by changing direction of auditory attention. Users with voluntary control of tensor tympani would also be able to control direction, speed and duration of movement of the interface by controlling the side, degree, speed and duration of contraction of the tensor tympani.

The current invention also describes how the detection of direction or side, or degree, speed or duration of voluntary movement of the ear-drum complex, is able to control variable interfaces to degrees relative to the degree, speed and duration of movement, providing dynamic control, which is not evident in the prior art.

The current invention is directed to an apparatus and method for controlling interfaces by detecting the ear-drum complex movements that are associated with intended movement controlled by eye movements or changes in voluntary auditory attention, and by the degree of voluntary ear-drum complex movement as intentional variable and/or graded or dynamic interface controls.

Detecting subtle movements of the ear-drum due to tensor tympani contraction will allow detection of the direction of intended auditory attention, and also may be decoded to enable detection of the specific frequencies of auditory interest.

One benefit of the current invention over existing hearing aids and hearing assistive devices, or hearable devices is that it detects a natural indicator of the direction and frequency of selective auditory attention, and enhances the user's hearing of those sounds of interest by selectively amplifying them. It therefore helps the user hear in the "cocktail party scenario" and provides general improved and more natural hearing ability. It provides this benefit by a sensor embedded in these devices which does not require a good electrical contact or external electrical contacts or wires. The incorporation of inputs from devices in both ears, allows cross referencing to prevent artifactual changes. These sensors are cheap, small and easily available and, so, easily incorporated into existing hearing aids, etc.

Within these devices and earphone sensors for monitoring hearing and ear-response to sound, the sensor may also provide the ability to monitor the response of the ear-drum to sound transmission from the device to allow monitoring of hearing ability and optimisation of the sound production in response to this. This allows a sound to be emitted from the device and the sensor to detect resultant movements and changes of the ear-drum including but not limited to frequencies of vibration, and/or resonance. This data may be acquired with one sound or single tone output, or averaged over a series of multiple sound outputs. The sound may be any combination of a single tone or sound, more than one different tone, and/or a combination of several different tones emitted at the same time, at a single or differing volumes, in one or both ears. Advantageously, sound amplification, a transmission profile, or other parameter of the hearing aid, etc. may be altered or adjusted by the algorithm of the processor to provide optimum or user-preferred sound transmission or reception. Further, where the hearing aid, etc. is wirelessly connected to another device including the function to alter the ear device settings, this would allow the other suitable device to adjust the sound amplification, transmission profile or other parameters with or without involvement of a healthcare or hearing care worker.

Embodiments incorporating the hearing aid, etc. wirelessly connected to the internet or a similar network, either directly or by connection to another internet connected device, would allow remote adjustment of the sound amplification, transmission profile or other parameters by a healthcare or hearing care worker, or by another algorithm of another processor remote to the user. This is an advantage over current hearing aids, etc. where adjustments can currently be made remotely only based on subjective measures of hearing loss such as audiograms.

Conversely, with the present invention which involves an objective measure of the physical response of the ear-drum to transmitted sounds, alteration of the output of these devices based on objective measures to increase the efficiency of sound transmission is made possible.

The present invention provides improved function of hearing aids, assistive hearing and hearable devices by incorporating natural control of selective auditory attention. It also allows more objective assessment and adjustment of hearing function by detecting response of the ear-drum to sounds.

BRIEF DESCRIPTION OF THE DRAWINGS

The invention will now be disclosed, by way of example only, with reference to the following drawings, in which:

FIG. 6 is a flowchart showing eye movement related control of a cursor graphical interface control of a VR headset device, by detecting ear-drum complex movements associated with eye movements;

FIG. 7 is a flowchart showing eye movement related control of a cursor graphical interface control of a AR headset device by detecting reciprocal ear-drum complex movements associated with eye movements, by sensor(s) located in earphone devices in each ear to provide more accurate control;

FIG. 8 is a flowchart showing a sensor which detects the degree and duration of ear-drum complex movement, and using an output to control the degree of control of an interface;

FIG. 11 is a flowchart showing a sensor detecting ear-drum complex and ear-drum margin movement thereby controlling lens focus of spectacles;

FIG. 12 is a flowchart showing eye movement related control of a cursor graphical interface control of a VR headset device, by detecting ear-drum complex movements associated with eye movements;

FIG. 13 is a flowchart showing eye movement related control of a robotic arm, by detecting ear-drum complex and ear-drum margin movements associated with eye movements and convergence by sensors located in earphone devices in each ear;

FIG. 16 is a flowchart showing a sensor detecting ear-drum complex and ear-drum margin movement, enabling the user to communicate by controlling an on-screen keyboard (graphical representation of a keyboard), by selecting text characters by eye-brow raise movements;

FIG. 17 is a flowchart showing selective amplification and output of speech frequencies from hearing-aids, assistive hearing or hearable devices, on the side of auditory attention by detecting ear-drum complex movements;

FIG. 18 is a flowchart showing the incorporation of information from two sensor outputs from hearing aids, assistive hearing or hearable devices, in both ears, to provide more reliable control of selective amplification of sound output from the device on the side of auditory attention;

FIG. 19 is a flowchart showing a sensor which detects the degree and direction of ear-drum complex movement, and using this output to control the degree of selective amplification of frequencies of the sound output of an earphone device to provide selective auditory focus on specific frequencies of sounds of auditory attention; and FIG. 20 is a flowchart showing the sensor detecting the degree and direction, and frequency of movements and/or resonance of the ear-drum complex, in response to sound emitted from the earphone device.

DETAILED DESCRIPTION OF THE INVENTION

Figure 14:
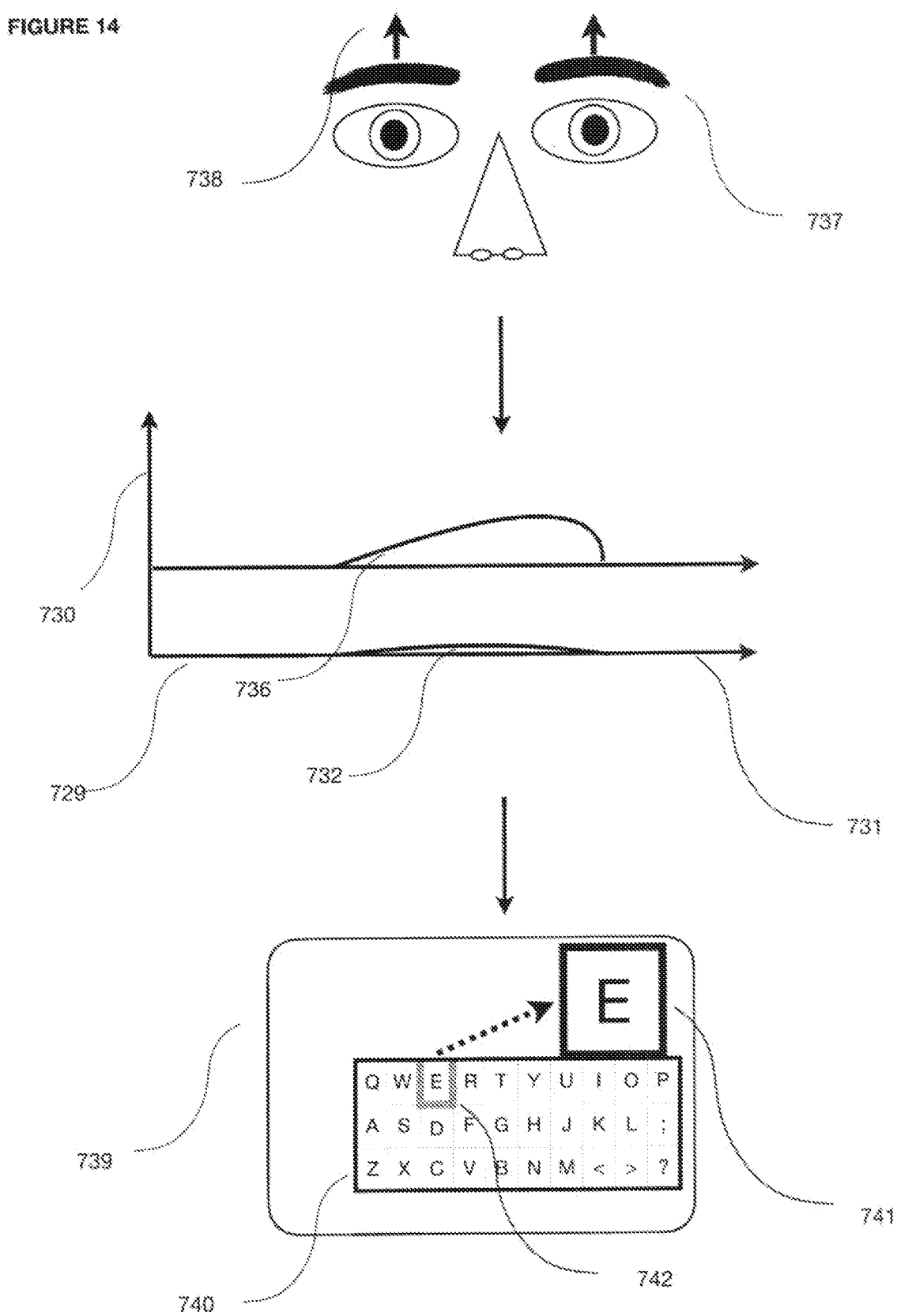
FIG. 14 is a graphical representation of recorded ear-drum complex movement, and of a section of ear-drum margin movement, in association with eye-brow elevation, as detected and analysed using an imaging sensor.
Figure 15:
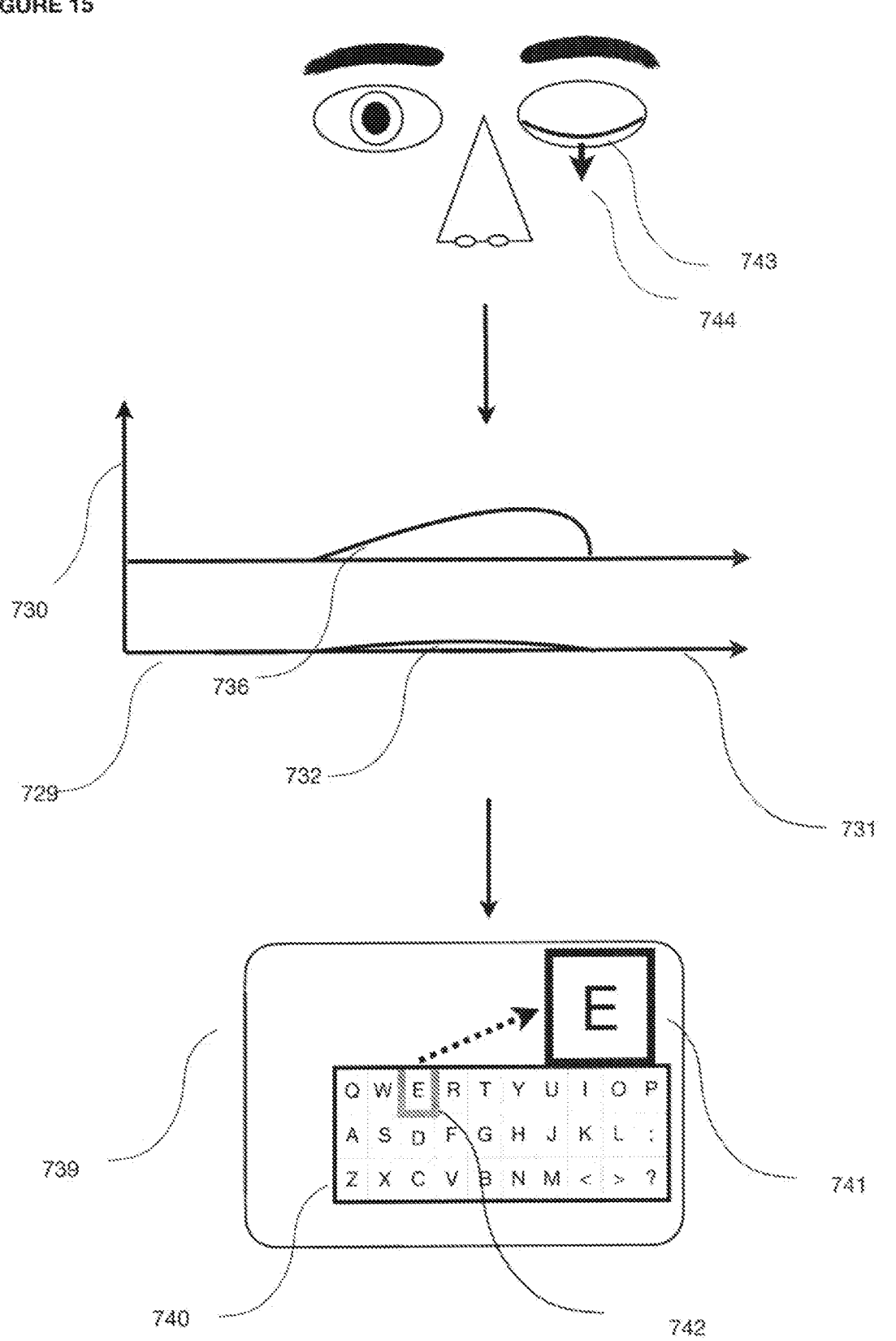
FIG. 15 is a graphical representation of recorded ear-drum complex movement, and of a section of ear-drum margin movement, in association with firm eye-lid closure, as detected and analysed using an imaging sensor.

A first embodiment of the present invention is disclosed in relation to FIGS. 1 to 8 and the corresponding description, FIGS. 1 to 4 being common subject-matter to each embodiment; a second embodiment is disclosed in relation to FIGS. 9 to 13 and the corresponding description; a third embodiment is disclosed in relation to FIGS. 14 to 16 and the corresponding description; and a fourth embodiment is disclosed in relation to FIGS. 17 to 20 and the corresponding description. As each embodiment includes the common subject-matter of FIGS. 1 to 4, once described in relation to the first embodiment, that subject-matter will not be described again save as to enable disclosure of specific features of relevance to the respective embodiment. Common references will be utilised for common features where possible.

The method for detecting changes of the ear structures of this invention, is, generally, the use of a sensor wholly or partially sited in or adjacent the ear canal. This sensor detects changes including changes in: distance from the sensor, position, movement, shape and/or colour of the ear drum complex, ear-drum margin and/or associated ear structures, or change in pressure within the ear-canal. The sensor detects changes which may occur during normal hearing.

The sensors of the invention include sensors which are imagers, including cameras, video cameras or laser detectors, using any combination of visible or non-visible spectrum light or infrared radiation, or ultrasound transducers and ultrasound sensors, including polyvinylidene fluoride film (PVDF) transducers. Additionally, or in the alternative, the sensor may include, but are not limited to, laser Doppler vibrometry, time of flight sensors or LIDAR, digital holography, optical coherence tomography and/or pressure sensors. These sensors detect movement or change of characteristics of the ear-drum complex, ear-drum margin and/or associated ear structures, and the data is transmitted to a processor or processors which detect movement of the ear-drum complex, etc. The information is communicated as an input to a processor that may be within the structure containing the sensor (earphone) or connected by wire or wirelessly to another device. An algorithm of the processor analyses the output data, and detects movement or change of characteristics of the ear-drum complex, ear-drum margin and/or associated ear structures by changes in the data over time. The sensor may have an associated light source, such as LED, emitting visible, non-visible or infra-red light, or laser or ultrasound emitter, located within the sensor structure or earphone. The use of infra-red imagers may avoid the need for a light source as the ear structures emit infra-red thermal energy that can be detected as images owing to body temperature.

The processor generates an output dependent upon the algorithm detecting a change of the ear-drum complex, which may include change in distance from the sensor, movement, position, colour, and/or shape of a part or whole of the ear-drum complex. The algorithm is configurable and may be programmed on an individual basis according to the specific sensor, application and user. This output from the processor controls or is communicated to another processor that controls the output to the users.

In a first embodiment, FIGS. 1 to 8 disclose and describe a sensor worn by a user in or adjacent the ear canal, with the sensor detecting movement of the ear-drum complex, which generates an output to control an interface dependent upon the degree of movement of the ear-drum complex detected.

Figure 1:
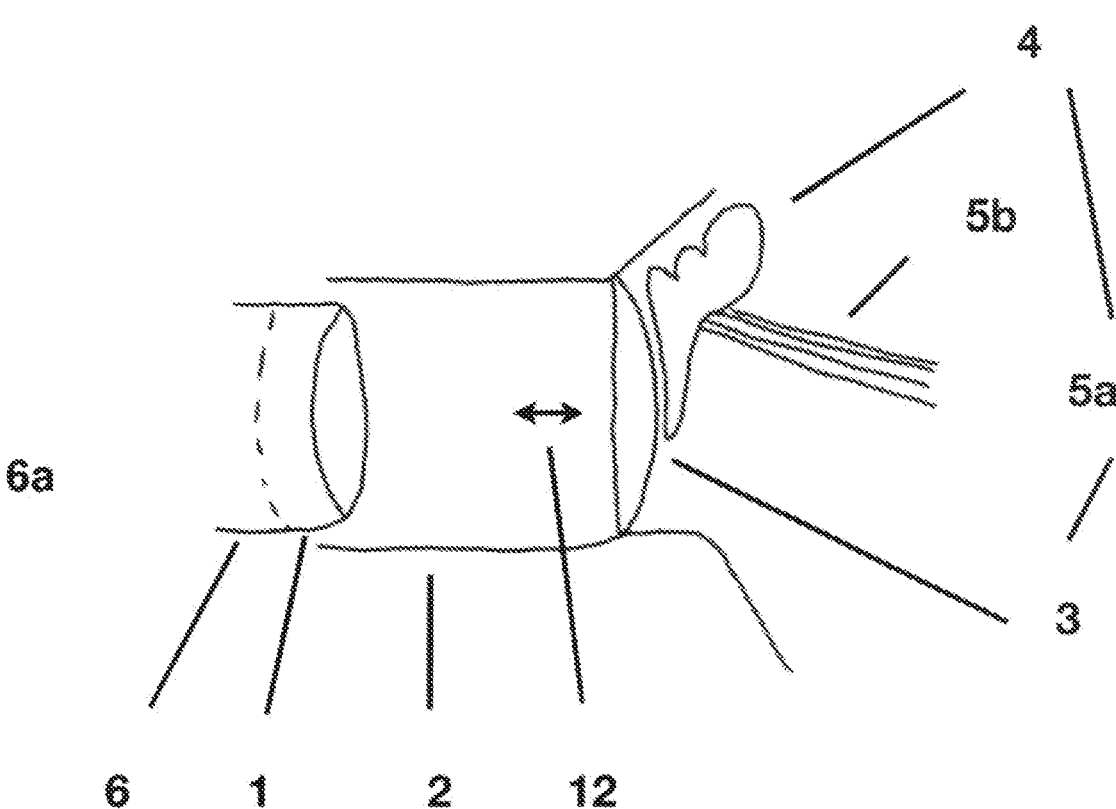
FIG. 1 is a pictorial representation of a cross section of the right ear canal and partial view of middle ear showing a sensor in the ear canal in relation to ear-drum, malleus and tensor tympani muscle.

FIG. 1 illustrates an example of the sensor 1 as a cross-sectional view of the right ear canal 2. The sensor 1 is located in the ear canal 2, with the sensor being part of an earphone, hearing aid or hearable assembly 6. For ease, these will hereinafter be referred to as 'earphone'. The sensor 1 is directed towards the ear-drum complex 5a, partially consisting of the ear-drum (tympanic membrane) 3 and the malleus 4 (a middle ear bone) that is connected to the inner aspect of the ear drum 3. The sensor 1 may have a configuration including an imager, which may be a video camera or an infrared video camera, with or without light source, or have a laser emitting and receiving combination which may have a static or scanning laser element (including laser Doppler vibrometry, optical coherence tomography, laser triangulation), time of flight or LIDAR sensors, or any combination of these. Alternative embodiments include the sensor being an ultrasound emitter and receiver complex, or a pressure detecting sensor. The tensor tympani muscle 5b attaches to the malleus 4. Movement of the ear-drum complex can be in any plane 12; 13 (in FIG. 2) and is detectable by the sensor 1. The earphone 6 houses one or more sensors 1, and may also house the processor including its algorithm—although both the processor and algorithm do not necessarily need to be located within the earphone and may work remotely.

Figure 2:
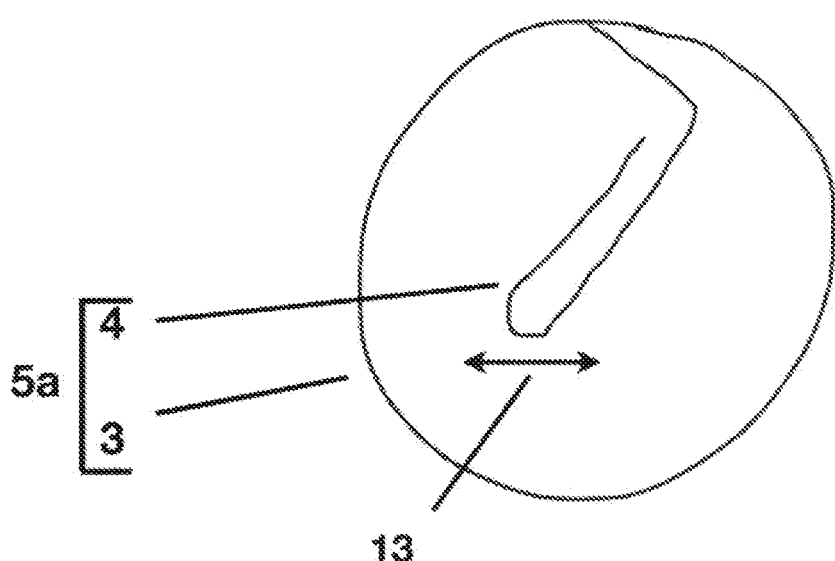
FIG. 2 is a schematic view of the external aspect of the right ear-drum showing an impression of the embedded malleus bone.

FIG. 2 illustrates an external view of the ear-drum complex 5a showing the ear-drum 3 and the malleus 4 which is visible through the ear drum 3, where it is located attached to the inner aspect of the ear-drum 3. A possible plane of movement of the malleus is shown by reference 13.

Figure 3:
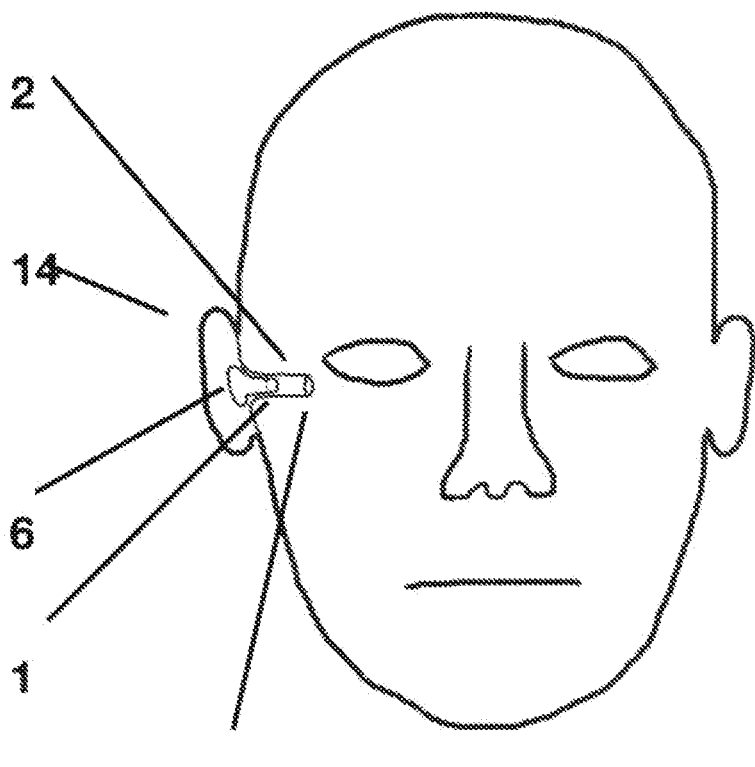
FIG. 3 is a pictorial representation of the sensor worn as a hearing-aid, assistive hearing, earphone or hearable device in the right ear canal.

FIG. 3 shows the sensor 1 configured in an earphone 6 with the sensor 1 being positioned (worn) partially within the ear canal 2, with the external aspect being located within the external ear, pinna 14. The sensor 1 is directed towards the ear-drum 3. Other embodiments include the sensor 1 being located in a structure totally within the ear canal 2 or situated (worn) within or adjacent the external ear 14, either as an individual structure or physically connected to a similar structure adjacent the other external ear 14.

Figure 4:
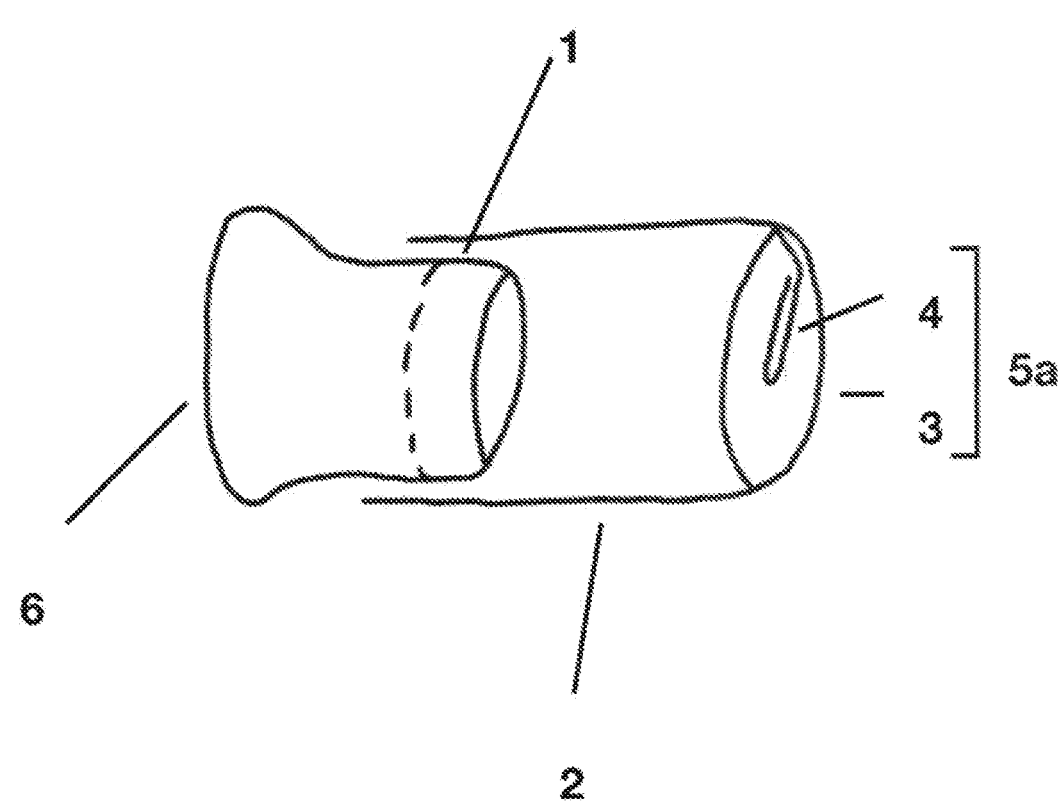
FIG. 4 is a pictorial representation of the ear sensor located partially within the ear canal close to the ear-drum.

FIG. 4 shows the sensor 1, within the earphone 6 partially sited within the ear canal 2, directed towards the ear-drum complex 5a, showing the ear-drum 3, and the malleus 4. Methods of detecting movement of the ear-drum complex, or change of shape, include detecting movement of the ear-drum complex 5a by a laser emitter and receiver, and other sensor methods and apparatus, including LIDAR or time of flight sensor within the earphone 6.

Figure 5:
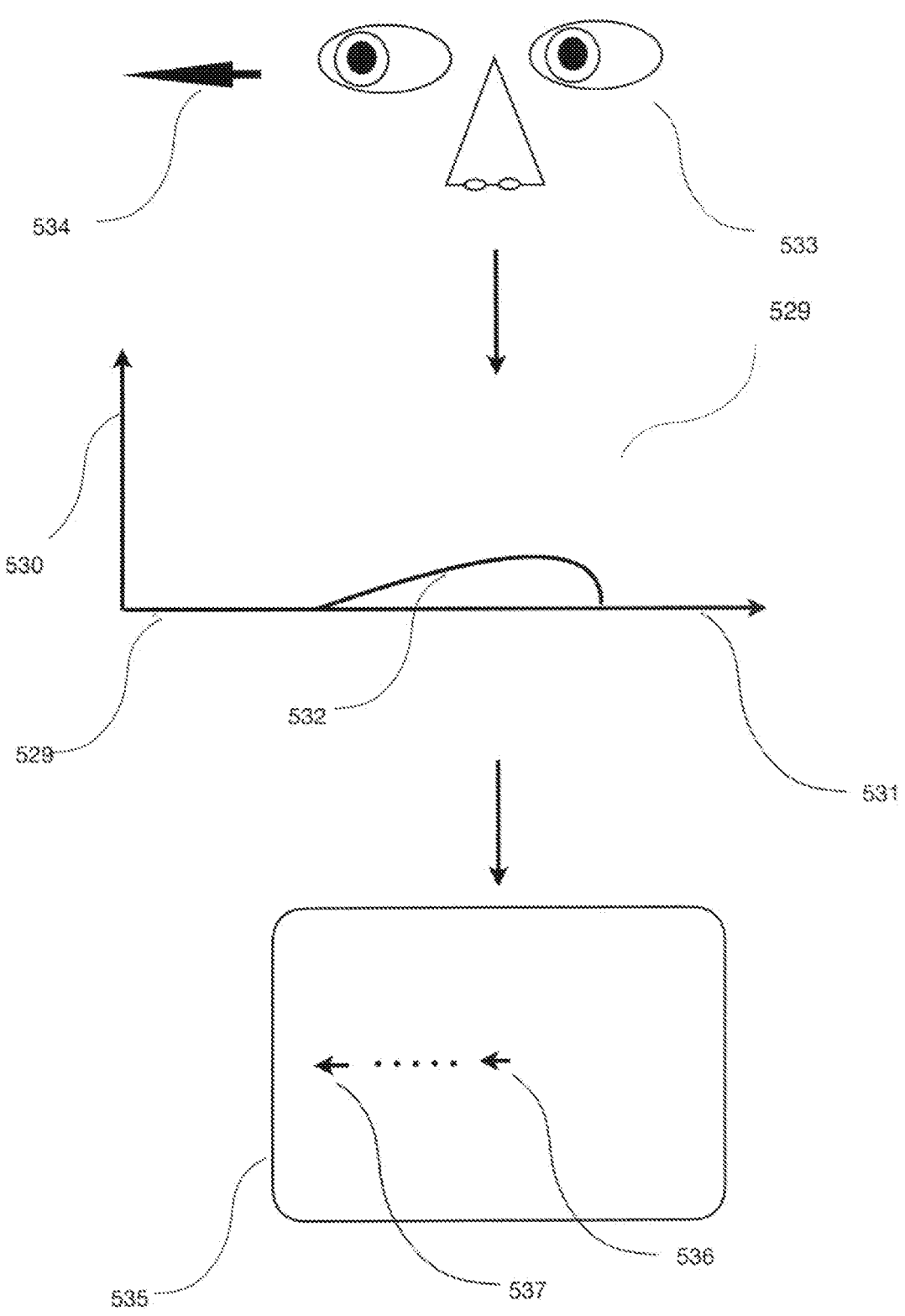
FIG. 5 is a graphical representation of recorded movement of the malleus with ear-drum complex movement in association with eye-movements, as detected and analysed using an imaging sensor to control movement of a graphical cursor on a screen interface.

FIG. 5 is a graphical representation showing measurement of ear-drum complex 5a as detected by sensor 1 being a video camera with associated LED light source within the earphone 6. In this example, the camera within the sensor 1 may use any fixed point, or area, on the ear-drum complex 5a to record movement 12; 13 and, for example, may record a position of the lower end of the malleus 4. This position and movement is detected by the video camera sensor 1 and the position is represented as a line on the graph 529, where the y axis represents the position and measurement of movement 530, and the x axis represents time 531. Movements 12; 13 of the ear-drum complex 5a are represented on the graph as line 532. In this representation, movement of eyes 533 to the left 534 is detected by the sensor 1 by detecting concurrent movement 12; 13 of the malleus 4 and the change of position (movement 12; 13) of the malleus 4 and the ear-drum 3 (ear drum complex 5a). This change of position of the malleus 4 detected by the sensor 1 is shown as a deflection of the line 532. As the eyes move to the left 534, the sensor detects movement of the left ear-drum complex owing to movement of the middle ear muscles contracting and displacing the malleus 4. As the movement is detected, a signal is output from the sensor 1 to the processor and its algorithm. The output of the processor effects a change in a graphical user interface 535. In this representation, the graphical user interface is a computer screen 535, and the output from the processor effects movement of the graphical cursor 536 in a horizontal plane to a new position 537 to the left of its original position. The processor and/or algorithm and/or graphical interface device 535 is/are configured so that movement of the cursor 536 is calibrated to coincide with the centre of gaze of the user. The cursor 536 is, therefore, moved around the screen 537 by eye-movements 534 which are detected by ear-drum complex movements 12; 13.

FIG. 6 is a flowchart showing the sensor 1 being within an earphone 6, and the sensor 1 detects movement 516 of the ear drum complex 5a. The output of the sensor 1 detecting the position and/or movement is transmitted to the processor within the earphone 6, or another device by wired or wireless communication 517. The processor effects a change in position of a graphical control icon ("cursor") on a graphical interface viewed on a VR head-set, determined by its algorithm which incorporates the data from movement of the ear-drum complex 518. When the algorithm receives data indicating that the left ear-drum moves away from the sensor, the algorithm effects a movement of the position of the VR headset cursor to the left, for example, to coincide with the eye-movements to the left associated with the reflex ear-drum movements 519. The degree and speed of movement of the cursor in an embodiment is controlled by the degree and speed of movement of the ear-drum complex relative to the sensor(s), and the duration in which the new position of the ear-drum is maintained 520. In a further example, the algorithm could be programmed by the user and calibrated such that a degree of movement of the cursor related to the ear-drum complex movements controls the graphical cursor to move to be at the fixed focus point of gaze and, so, replicate eye-tracking control 520.

FIG. 7 is a flowchart showing the sensor 1 within an earphone 6. The output from the sensors 1 and/or processor in each of two earphones worn by a user are communicated to a processor of an earphone 6 worn in an opposite ear of the user, or to a processor of another device by wired or wireless communication method 521. The output of its algorithm detects the difference between movement of each ear-drum complex of the user towards or away from the respective sensors, and controls the degree and direction of movement of a graphical cursor 522. Movement of the graphical cursor 522 is more accurate in detecting reciprocal movements of the ear-drum complex associated with eye-movements, and this increases the reliability of accurately replicating eye-movements and maintaining the graphical cursor at a centre of the user's gaze 523.

FIG. 8 is a flowchart showing a process for detecting ear-drum complex movement and providing an output to a processor in the earphone 6 by wired or wireless communication. The sensor 1 detects the position, amplitude, degree and direction of the ear-drum movement, and the output signal incorporates information on such position, amplitude, degree and direction of movement the ear-drum complex, which is transmitted to the processor of the earphone 6 by wired or wireless communication 524. The algorithm controls the amplitude or degree of a variable interface in a degree relative to the amplitude/degree, speed, direction and/or duration of the sustained movement 525. Such that, the output from the processor controls a graphical interface where the graphical interface is a graphical "slider" that controls volume of sound output of a device 526. A prolonged sustained movement of the ear-drum effects a movement of the graphical slider of the interface device, and effects an increase in volume of the sound output from a connected device directly proportional to the movement of the graphical slider movement 526. This method allows a user of the earphone to voluntarily control a user interface in a variable manner, by variable and voluntary movement of the ear-drum complex.

The desired function, such as movement control of electric wheelchair, may be activated by a control signal, detected by sensors claimed in this invention; for example two short duration ear-drum complex movements in rapid succession. This would prevent eye-movement or auditory attention during normal activity triggering a change in the interface or connected device, such as movement of an electric wheelchair, when it is not intentionally desired by the user.

A further advantage over existing controls or sensors is that the location of the sensor wholly or partially in the ear canal fixes the position of the sensor relative to the ear drum position. With involuntary or voluntary head or neck movements, the relative position of the sensor to the ear-drum position does not change, and so the sensor reliably detects movement of the ear-drum complex irrespective of background head or neck movements. This allows accurate sensing of the triggering ear-drum complex movements in people who are unable to control head movements, or have involuntary movements, and/or when other movements complicate the detection of trigger movements, such as in vehicles and during other motion. The sensor is operated hands-free and, so, does not rely on a user having control of their limbs, or interrupting other activities, such as operating machinery or vehicles.

Advantageously, the output from the sensor or processor may be integrated, by the algorithm of the processor, with an output from other sensors such as eye movement detection sensors or accelerometers detecting head movement to effect a change in the user interface. This allows several modalities or locations of sensors to improve accuracy of control, including, but not limited to moving a graphical cursor of an interface with the position of eye gaze, which embodiment includes incorporating vertical movement of a graphical cursor by accelerometers affected by head movements.

Advantageously, the sensor may control hearing aid function to include dynamically increasing or decreasing volume, in relation to the duration and degree of ear-drum movement.

Advantageously, the invention provides silent and invisible control of mobile phones, communication devices, home management devices and entertainment devices, and any other device or processor applications, that can be triggered by a user interface, through short-range wireless communications, such as Bluetooth®, or through other links from the sensor to these devices. The ear-drum complex sensor can be used and worn like a hearing aid or earphone, or other earphone device, in or adjacent to the ear canal, and can be incorporated into other existing technologies such as hearing aids, earphones, and multi-function ear devices which may include a plurality of functions including telephone and entertainment audio play back, a microphone for telephone, voice communication and voice commands, accelerometers, pulse oximetry, temperature sensors and any other sensors. This provides a means of silent and invisible and variable/dynamic control of these and other user interfaces.

Detection of different duration ear-drum movements allows communication using connected interfaces such as radios or mobile phones, such as by Morse code.

By incorporating a microphone in the earphone containing the sensor, this enables the processor to process an input from the sensor in conjunction with an input from the microphone. The algorithm of the processor is configurable to exclude movement of the ear structures in response to external noises, from triggering an output signal, by excluding eardrum complex movements from generating an output when these are simultaneous with external noise of defined quality or volume detected by the microphone.

This invention provides a previously undescribed apparatus and method for controlling interfaces and devices from earphones, providing hands-free, silent and invisible control of interfaces and directional control related to eye-movements or directional auditory focus, and providing a previously undescribed method of dynamic and variable control of interfaces by voluntary movements of middle ear muscles.

In a second embodiment, FIGS. 9 to 13—in addition to the subject-matter of FIGS. 1 to 4—disclose a sensor 1 worn by a user in or adjacent the ear canal 2, with the sensor 1 detecting ear-drum complex 5*a* and/or ear-drum margin 3 and/or other ear structure movements or changes, which movements correspond to eye-convergence, vertical and/or horizontal eye movement, to generate an output to control an interface dependent upon changes detected.

Figure 9:
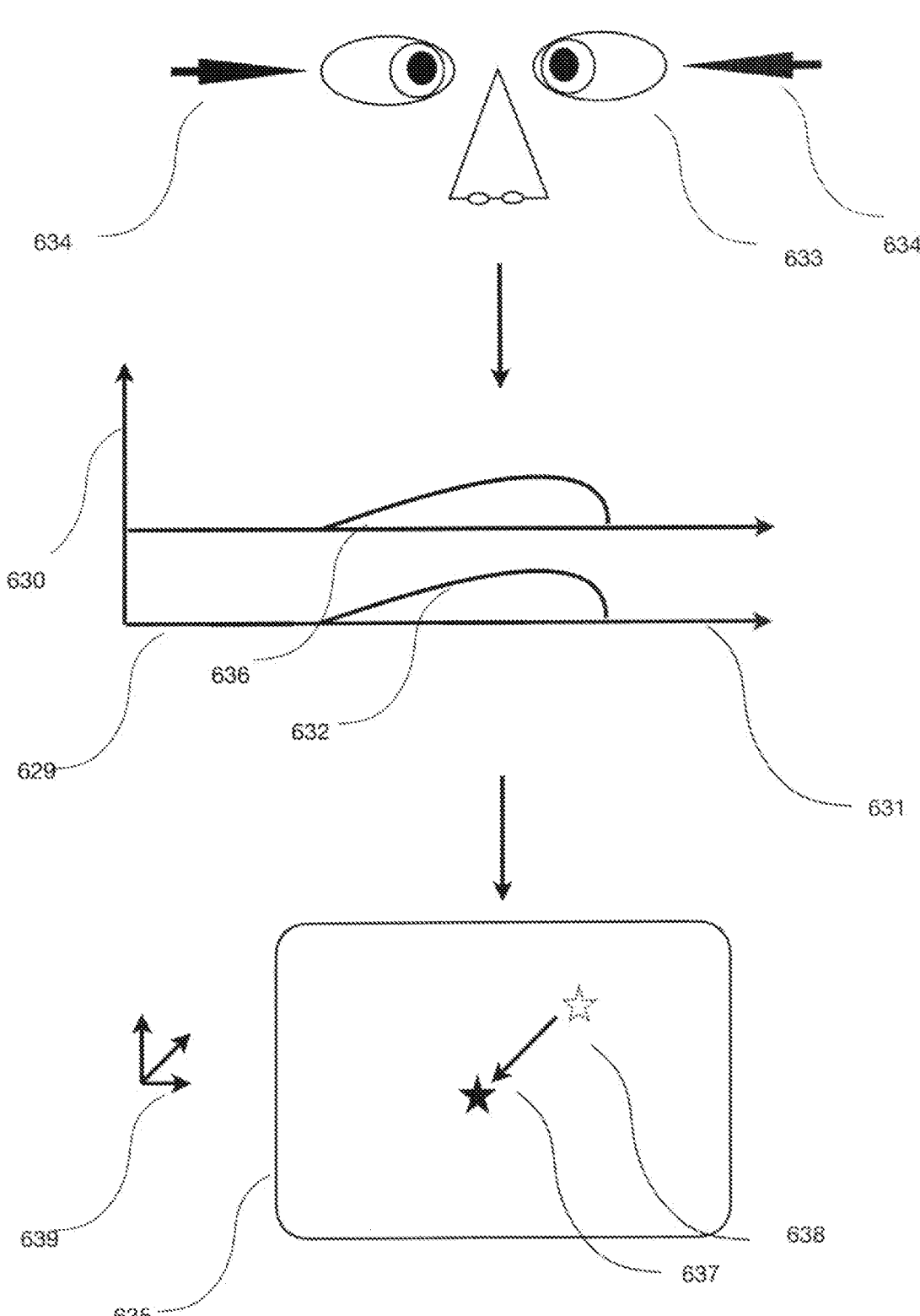
FIG. 9 is a graphical representation of recorded ear-drum complex movement, including a section of ear-drum margin movement, associated with convergent eye-movements, as detected and analysed using an imaging sensor, capable of controlling virtual three-dimensional movement of a graphical cursor on a stereoscopic screen interface, such as a VR device.

FIG. 9 is a graphical representation showing measurement of movements of the ear-drum complex 5*a* and the margin of the ear-drum 3 detected by the sensor 1, being a video camera with associated LED light source within the earphone 6. The camera within the sensor 1 may use any fixed point, or area, on the ear-drum complex 5*a* and/or ear-drum 3 margin to record movement 12; 13 and, for example, may record a position of the lower end of the malleus 4, and/or any section or length of the ear-drum 3 margin. The position and movement of any of these structures is detected by the video camera sensor 1 and the position is represented as two lines 632; 636 on the graph 629, where the y axis 630 represents the position and measurement of movement, and the x axis 631 represents time. Movements 12; 13 of the ear-drum complex 5*a* are represented on the graph as line 636 and movements of a lower posterior section of the ear-drum 3 margin are represented on the graph as line 632. Convergent movement 634 of eyes 633, when the user focuses on a near real- or virtual-object 637, is detected by the sensor 1, by detecting concurrent 12; 13 movement of the malleus 4 and the change of position (movement 12; 13) of the malleus 4 and the ear-drum 3 (ear drum complex 5*a*), and the sensor 1 also detects concurrent movement of the section of ear-drum 3 margin. This change of position of the malleus 4 detected by the sensor 1 is shown as a deflection of the line 636, and the change in position of the ear-drum 3 margin is shown as a deflection of the line 632. As the eyes converge 634 during the act of the user focusing on a near-object 637 from focus on a far-object 638, the sensor 1 detects movement of the ear-drum complex 5*a* and of the ear-drum 3 margin. As the movements are detected, a signal is output from the sensor 1 to the processor and its algorithm. The output of the processor is dependent upon a comparison between ear-drum complex 5*a* movement and ear-drum 3 margin movement, and effects a change in a graphical user interface 635. In this example, the graphical user interface is a display of a virtual reality headset representing a three-dimensional scene with a foreground/near-focus virtual object 637. The output from the processor effects a movement of a virtual graphical cursor, in a virtual three-dimensional manner, from its starting position corresponding to the far-object 638 to a new position corresponding to near-object 637.

The processor and/or algorithm and/or graphical interface device 635 is/are configured so that concurrent movements of both the selected area of ear-drum 3 margin and the ear-drum complex 5*a* consistent with eye-convergence effect movement of the cursor which is calibrated to coincide with the centre of gaze of the user, together with the depth of focus of the user on the three-dimensional virtual scene. The virtual cursor is, therefore, moved around the rendered virtual three-dimensional environment in any virtual three-dimensional plane 639 by eye-movements 634 detected by ear-drum complex 5*a* and ear-drum 3 margin movements 12; 13 corresponding to the area on the screen or virtual object on which the user is visually fixated and has visual focus.

Figure 10:
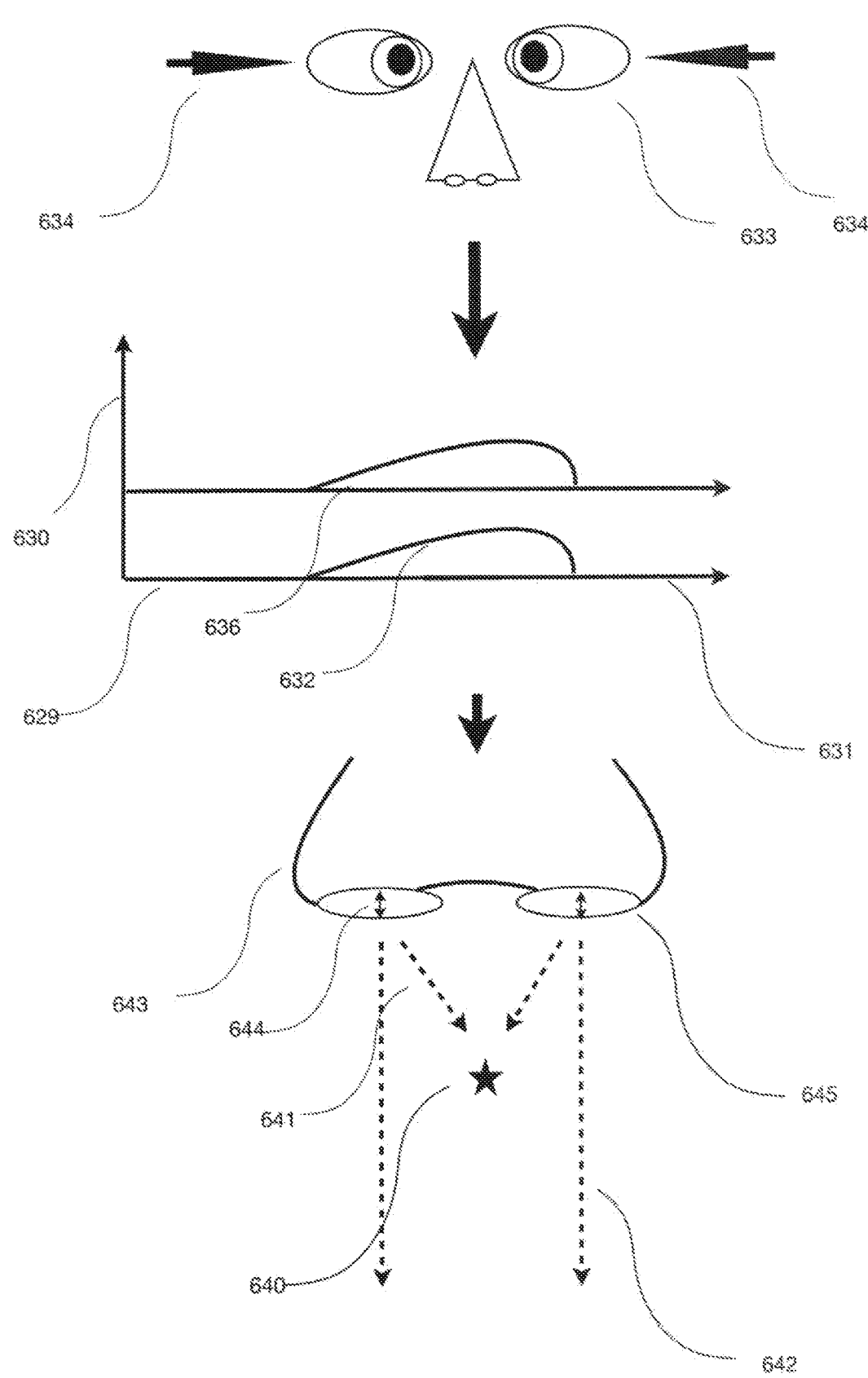
FIG. 10 is a graphical representation of recorded ear-drum complex movement, including a section of ear-drum margin movement, in associated with convergent eye-movements, as detected and analysed using an imaging sensor, capable of controlling optical power of lenses of spectacles.

FIG. 10 is a graphical representation showing measurement of movements of the ear-drum complex 5*a* and the margin of the ear-drum 3 detected by sensor 1, in which sensor 1 is a video camera with associated LED light source within the earphone 6. The camera within the sensor 1 may use any fixed point or area on the ear drum complex 5*a* and/or ear-drum 3 margin to record movement 12; 13 and, for example, may record a position of the lower end of the malleus 4 and/or any section or length of the ear-drum 3 margin. The position and movement of any of these structures is detected by the video camera sensor 1 and the position is represented as two lines 632; 636 on the graph 629, where the y axis 630 represents the position and measurement of movement, and the x axis 631 represents time. Movements 12; 13 of the ear-drum complex 5*a* are represented on the graph as line 636, and movements of the lower posterior section of the ear-drum 3 margin are represented on the graph as line 632. In this example, convergent movement 634 of the eyes 633, when the user fixes its gaze 641 on a near real object 640, is detected by the sensor 1, by detecting concurrent 12; 13 movement of the malleus 4 and the change of position (movement 12; 13) of the malleus 4 and the ear-drum 3 (ear-drum complex 5*a*) and by also detecting concurrent movement of the section of ear-drum 3 margin. This change of position of the malleus 4 detected by the sensor 1 is shown as a deflection of the line 636, and the change in position of the ear-drum 3 margin is shown as a deflection of the line 632. As the eyes converge 634 during the act of the user focusing on the near-object 640 from focus on a far-object 642, the sensor 1 detects movement of the ear-drum complex 5*a* and of the ear-drum 3 margin. As the movements are detected a signal is output from the sensor 1 to the processor and its algorithm. The output of the processor is dependent upon a comparison between malleus 4 movement and ear-drum 3 margin movement and effects a change in optical characteristics of a lens 645 of spectacles 643. The user interface is, effectively, spectacles worn for near-641 and far-642 focus, and the output from the processor effects a change in the variable optical power of (opto-electronic) lenses 645 of the spectacles 643 worn by the user. The processor and/or algorithm, and variable focus lenses 645, are configured so that concurrent movements of both the selected area of ear-drum 3 margin and the ear-drum complex 5*a*, consistent with eye-convergence 634; 641, effect a change in the optical power 644 of the lenses 645 to a power that provides focus 641 at the distance of the object 640 to which the user is fixing its gaze. In this example, the processor causes the lenses 645 to become more convex 644 enabling focus on a near object 640. The spectacles 643 may, therefore, automatically change optical power 644 so the user can change focus from objects at variable distances, enabling good acuity vision for both far-objects 642 and near-objects 640 (such as for focusing on text of a book whilst reading).

FIG. 11 is a flowchart providing a process for detecting ear movements and output to a processor in the earphone 6 by wired or wireless communication 616. The sensor 1 detects the position, amplitude/degree, and direction of the ear-drum complex 5*a* and ear-drum 3 margin movement, and the output signal, which incorporates information on the position amplitude/degree and/or direction of movements of the ear-drum complex 5*a* and ear-drum 3 margin, is transmitted to the processor of the earphone 6 by wired or wireless communication 624. The algorithm of the processor effects a change in the optical power of variable optical power lenses in spectacles worn by the user 625. The output from the processor is configured to change the optical power of the spectacle lenses to match the distance of the object that the user has visually fixed with its gaze; the optical power of the lenses provides visual focus on the object by correcting visual acuity that is affected by presbyopia 626. This method allows a user of the earphone 6 to automatically focus on near- or far-objects with variable focus spectacles.

FIG. 12 is a flowchart showing the sensor 1 being within an earphone 6, and the sensor 1 detects movement 616 of the ear drum complex 5*a* and ear-drum 3 margin. The output of the sensor 1 detecting the position and/or the movement is transmitted to a processor within the earphone 6 by wired or wireless communication 617. The processor effects a change in position of a graphical control icon (i.e. a cursor) on a stereoscopic graphical interface viewed on a VR head-set display as determined by an algorithm which utilises the data from movements of the ear-drum complex 5*a* and/or ear-drum 3 margin and/or other ear structures 618. If the algorithm receives data indicating that the left ear-drum moves away from the sensor, the algorithm effects a movement of the position of the VR headset virtual cursor to the left, corresponding with eye-movements to the left as detected by associated ear-drum complex and ear-drum margin movements 619. The algorithm effects movement of the virtual cursor in three-dimensions; with two dimensions of control related to horizontal and vertical eye movements, and virtual depth of the virtual cursor control related to convergence of eyes during fixation of gaze on a virtual stereoscopic location. The algorithm of the processor also effects an optical change in the variable optic display of the VR device relative to depth of intended focus of the user. So, this replicates physiologically matched accommodation and convergence of the eyes 620.

FIG. 13 is a flowchart showing the sensor 1 within an earphone 6; 16. The output from the sensors 1 and/or processor(s) in each of two earphones worn by a user are communicated to the processor of the device worn in the opposite ear of the user, or to a processor of another device, by wired or wireless communication method 617. The output of the algorithm is affected by movements of each ear-drum complex and of the ear-drum margin of each ear to effect the movement of a prosthetic robotic arm and hand 622. The algorithm is configured such that the prosthetic robotic arm is controlled to move the attached robotic hand to a position adjacent the three-dimensional location of the centre of the users focus and gaze 623. This enables control of the robotic hand to grasp an object.

The sensor effects, via a processor its algorithm, control of interfaces to include: control of variable focal power of lenses; provide vergent congruent accommodation and visual focus directed selection (i.e. for AR & VR interfaces); three-dimensional control of interfaces including virtual interfaces and mobile devices and robotics; enhanced accuracy of attention driven directional auditory focus; interface switches controlled by ear structure movements associated with eye movements; and monitoring of ear-drum complex, ear-drum margin movement and other ear structure movements as a biometric measure of health, disease, physiological and behavioural activity.

Advantageously, the present invention relates to a sensor that detects movements associated with eye-movements in two dimensions and depth of intended visual focus, and/or direction of auditory focus, which may include imagers and other sensors, located in the earphone. These sensors are not affected by talking, eating, chewing or other facial or head movements, or external movements, and are not dependent on a sealed ear-canal. The invention provides accurate two dimensional eye-tracking without the need for eye imagers, including accurate vertical as well as horizontal movement tracking.

None of the prior art has been able to detect central movement of eyes, or detect the intended focus of the user (focal depth, and/or accommodation), which is associated with bilateral medial movement of the eyes towards a central focal point (convergence). The present invention provides such an apparatus and method for detecting eye convergence from earphone sensors, providing at least one extra dimension of control-three-dimensional control of interfaces.

Video analysis of ear-drum complex and ear-drum margin movements in relation to the sensor, and dynamic measurements of movement of the ear-drum complex and ear-drum margin associated with eye-movements, show that, during convergent eye movements (for example when a user focuses on an object near to the face, such as during reading), a section of the ear-drum complex margin moves in association with the movement of areas of the ear-drum, including in association with movement of an area near the end of the malleus (from an in-person observation). This movement is of different character to movements of these structures related to: voluntary tensor tympani control; horizontal eye movements, where, for example, the area of ear-drum near the end of the malleus may move backwards independent of ear-drum margin movement; or vertical eye movement, where, for example an area of the ear-drum near to the end of the malleus moves upwards, independent of movement of the ear-drum margin.

Various combinations and types of movements of different areas of the ear-drum complex and ear-drum margin define specific user activities or movements, to include, for example vertical eye movement, convergent gaze, voluntary movement, return of eye gaze to central gaze and/or directional auditory attention. This invention includes both the ability to track eye convergence as a function of near- or far-, or change of-, visual focus, and provides a method of more accurate eye-tracking or auditory attention tracking by incorporating data on both the ear-drum complex movement (often effected by the middle ear muscles) and ear-drum margin movements, and/or other ear structures, which may be affected by other movements (such as external ear muscle movements). Additionally this provides the ability to locate eye-focus in eye positions including central and other eye positions. Relative differences in changes between the movement in both ears provide information on the location and depth of visual focus which may be positioned centrally, or away from the midline position, for example when the user is focusing on a point that is away from the central eye position (i.e. if the user moves its eyes and focuses on a point that may be to the right of the vertical plane and above the horizontal plane).

The processor and its algorithm provides more accurate information and three-dimensional analysis and detection of eye movements, direction of auditory attention, and position and depth of intended visual focus.

Movement of the ear-drum margin is considered to have causes which include: movement of the cartilage of the ear canal by action of the external ear muscles; the *auricularis* anterior, *auricularis* posterior, *auricularis* superior, and the muscles of the pinna; the *helicis* major, *helicis* minor, transversus *auriculae, obliquus auriculae, tragicus* and anti-tragicus. These muscles act to move the pinna in different directions and so apply movement to different aspects of the cartilage of the ear-canal which is continuous with the ear-drum margins.

Visual analysis of the ear-drum complex and surrounding structures, using sensors of the current invention, show that the ear-drum complex and ear-margin movements are not generated by facial movements/speech/swallowing and head movements.

The present invention provides an apparatus and method for both eye tracking to control the displayed interface, and for controlling varifocal or multifocal display to: prevent vergence-accommodation conflict; and identify the virtual or real object that the user is attending to/focusing upon. This allows the user's gaze focus to control the interface according to the depth of the users focus on a salient feature. For example a projected graphical user interface may have several virtual objects located within the same visual direction but at different virtual stereoscopic depths. Detecting depth of the user's intended focus by detecting the convergence angles of the eyes to focus on the virtual objects enables the user interface to provide user-controlled output dependent upon which virtual object is focused on by the user. For example, the user interface may present a visual text label associated with the virtual object that is focused on by the user.

The present invention controls the focus of spectacles, for example in users with presbyopia. The sensor of the current invention in earphones detect ear-drum margin and/or ear-drum complex and/or other ear structure movements linked to degree of convergence of the eyes during change in intended distance of optical focus. The data from the sensor is communicated to a processor, and algorithm of the processor effects a change in variable focus lenses to match refractive index (optical power) to the intended distance of focus. This allows the user to clearly focus at the appropriate distance by, for example, correcting for presbyopia and allowing the user to focus on text on a page, or altering focus or magnification on a target with other optical instrument, such as automatically magnifying images in surgical operating spectacles or eye-wear. Embodiments include dynamically changing lens focus and also binary change between a single "far vision" optical power of the lens and a single "near focus" optical power of the lens in a bifocal arrangement. The latter requires only the detection of a convergence in a similar way to a switch signal to switch from the far-focus state to the near-focus state. In a further similar embodiment, the detection of eye convergence associated with in-ear movements triggers a subsequent interface that controls the optical power of the lens according to the distance from the spectacles to an object—this distance being detected by a range detector or other distance detector, such as time of flight device or any other sensor or device.

Other embodiments control remote auto focus of contact lenses and intra-ocular lens implants by detecting eye convergence related movements from the ear-drum complex, ear-drum margin and/or ear-related structures.

This enables development of narrow form spectacles and near-eye displays, including optically tunable spectacles and other similarly worn devices, because these do not rely on front mounted cameras that require line of sight and be positioned a suitable minimum distance from the eyes to accurately triangulate and detect eye convergence angle, or inter-pupillary distance.

Three-dimensional information on position of eye gaze and intended focus is used to control the three-dimensional movement and action of mechanical and/or virtual devices, for example the position, action and/or movement of a robotic arm. The sensor detects movement associated with eye movements in both horizontal and vertical planes, and/or direction of auditory attention, by ear-drum margin and/or ear-drum complex movements and/or other ear structure movements. These movements are communicated to a processor and algorithm of the processor effects movement of the robotic arm in horizontal or vertical plane in direct relationship to the direction and position of eye-gaze and/or auditory focus. Similarly the sensor or sensors detect ear-drum margin, and/or ear-drum complex movements, and/or other ear structure movements, related to the degree of convergence of the eyes. These movements are communicated to a processor and its algorithm to effect movement of the robotic arm in an additional plane, such as towards or away from the user, or effects a different action such as opening or closing a robotic hand. A haptic actuator within the earphone may provide feedback to the user, such as degree of pressure detected by sensors within the robotic fingers attached to the robotic hand and arm to enable the user to control the degree of pressure exerted on an object that is grasped by the robotic hand. Accordingly, the invention provides three-dimensional, or other movement or functional control of a prosthetic limb or robotics device by individuals with amputation(s), or by individuals with reduced, limited or absent movement (such as with locked-in-syndrome).

Further, the invention provides three-dimensional and/or multi-functional control of any virtual or physical interface, tool, mobility device, vehicle, or any other interface, which may be near to or remote to the user, that is a more reliable reflection of any three-dimensional change in auditory or visual focus or movement, than any previously described control interfaces detecting eye tracking or ear-movement detection.

Data reflecting ear-drum margin movements, and/or ear-drum complex movements, and/or other ear structure movement, that is detected by the sensor is transmitted to the processor enabling the algorithm to provide changes to the interface that more accurately reflect the user's eye-movement, or intended auditory of visual attention or focus, than in the prior art. Data from the sensor provides information to the algorithm that interprets this as health and/or physiological and/or disease and/or behavioural related data, to include, but not limited to, degree of compliance of the ear-drum, such as in: oto-sclerosis, glue ear and ear-drum perforations; abnormal movements or tremors, such as in dyskinesia, tensor tympani spasm, Parkinson's disease, athetoid cerebral palsy, cerebellar conditions and epilepsy; weakness such as in Guillain Barre syndrome, motor neurone disease (ALS), and myaesthenia gravis; degree of awareness or consciousness, such as in locked-in-syndrome, persistent vegetative states, anaesthesia, dissociative seizures; ability to achieve visual focus and/or attention including in neonates, children and adults; and/or any other disease monitoring or biometric measure or behavioural measure detected by analysis of ear-drum margin or ear-drum complex or other ear structure movements.

The method for detecting changes of the ear-drum complex and ear-drum margin and other ear structures in this invention is, generally, the use of a sensor wholly or partially sited in, or adjacent the ear canal. This sensor may be located in a structure worn like a hearing aid, hearing-assistive device, ear phone, "smart earphone" or "hearable" device, or earplug, or any in-ear device (subsequently jointly referred to as 'earphone'). This sensor detects changes of the ear-drum margin and/or ear-drum complex and/or other ear structures, to include the distance from the sensor, position, movement, shape or colour of the ear drum complex and/or ear-drum margin and/or other ear structure, or change in pressure within the ear-canal.

Where the earphone device also has a voluntary ear-drum control switch functionality, a further level of control from ear-drum complex and/or ear-drum margin and/or associated ear structure movement or change is provided. The combination enables the user to highlight, and activate or choose, a specific control, icon or other virtual object. By way of example, this could include directing a graphical cursor to a graphical icon, virtual object, or control setting and the switch "click" function subsequently selecting or activating the function of that icon/object and/or control.

The algorithm of the processor may analyse a two dimensional image of the ear drum, ear-drum complex, etc. and detects movement of the ear-drum margin and/or the adjacent auditory canal and/or the ear-drum complex, and/or other ear structures, by changes in the image over time (image analysis). This image analysis may be individually configured according to the sensor or sensors involved, to detect movement of the whole, or of any area of the ear-drum complex and/or any area of ear-drum margin and/or associated ear structures. For example, this may be a movement of a defined fixed point such as the lower end of the malleus, but may be any defined structure or reflection (the light reflex) on the ear-drum complex, or the adjacent auditory canal or ear-drum margin, or other ear structure.

The sensor may be within the ear canal, or located adjacent the outer ear, with the image relayed to the sensor by conduits of light from the ear canal, such as by fibre-optics.

The processor generates an output dependent on the algorithm detecting a change of the ear-drum margin, and/or adjacent auditory canal, and/or ear-drum complex and/or other ear structures, which may include: change in any combination of: distance from the sensor; direction of movement; degree of movement; position; shape, of part or the whole of the ear drum complex or ear-drum margin or associated ear structures or other ear structure; change in pressure in the ear canal; or other measure indicating movement of the ear-drum margin, and/or the adjacent auditory canal and/or ear-drum complex and/or other ear structures, or other characteristics including colour. The algorithm is configurable and may be programmed on an individual basis according to the specific sensor or sensors, application and/or user.

Algorithms may include those related to, and/or developed, and/or altered and/or affected by artificial intelligence and/or machine learning methods. These algorithms correlate any ear-drum complex and/or ear-drum margin, and/or other ear structure movements, in one or both ears, to determine relevant changes in any of eye-gaze location, distance of intended eye focus, and/or position of intended auditory attention, and, subsequently, control interfaces in several dimensions to include vertically and/or horizontally (for example in a coronal plane), and/or to include antero-posteriorly (at 90 degrees to the coronal plane), and/or variable lens or optical focus, and/or directional selective amplification of sound pitch and/or direction of sound. These algorithms may incorporate information from populations and/or the individual user over time to affect the algorithms. Algorithms for control interfaces may be located within processors within the earphones and/or within mobile phones, head-sets, including AR or VR devices, spectacles, surgical operating head-sets or spectacles, any wearable device, or other wired or wirelessly connected device.

The output of the algorithm is communicated to a device to trigger a change in the state of the device, which includes control of any digital, electronic or other device, including graphical cursor or target, or other similar graphical movement interface, or virtual object, including on computer or phone screens, AR or VR headsets, or any near-eye, head mounted or heads-up or similar displays, spectacles, surgical operating headsets or spectacles, robotic device including, but not limited to prosthesis, industrial or other robotic device, including devices remote to the user, remotely focusable contact lens or intra-ocular lens, or any other electronic interface or device. This output from the processor controls, or is communicated to another processor that controls, movement or change in the connected interface to include, but not limited to variable control of the degree and directionality of the device interface in response to the corresponding movements of the ear-drum complex and/or ear-drum margin and/or associated ear structures. The output may be controlled by movements or changes of the ear-drum and/or ear-drum margins and/or other ear structures, on the same side or, also in addition, by movements or changes communicated from a similar device in the opposite ear. This output may control position or movement, including of a graphical interface such as a three-dimensional representation of a graphical cursor, or two- or three-dimensional control of a mobile device such as a wheelchair or other vehicle, or of a device such as a robotic arm or limb or other prosthesis or assistive robotic device, or virtual movement within a graphical menu, or virtual movement in a virtual or augmented reality scene or rendered graphical interface.

The output from sensors from two ear-phone devices both provide input data to the algorithm of the processor. This enables the processor and its algorithm to change the user interface in relation to a difference and/or similarity between simultaneous movements of the ear-drum complexes and/or ear-drum margins and/or ear structures detected on both sides (i.e. from both ears). This comparison provides data indicating the relative eye convergence during near focus and alters user interfaces in relation to the relative eye convergence. This enhances the reliability of the control of the interface by producing more validated control based on confirmation of the relative movement of the ear-drum complexes. Further, this provides cross-referencing of data from each side to prevent artifactual changes, and effect specific control dependent on differences or similarities of the qualities of the signal from each side. The output from the sensors from each ear may be transmitted by wire or wireless communication to the earphone processor in either or both devices, and to other devices including, but not limited to a mobile phone, computer, VR and AR or other near-eye displays or headsets, mobile devices, robotic devices or any other interface.

When a user moves its gaze (visual focus) away from the midline to one side of the head, the sensor detecting the movement of the drum on the same (ipsilateral side) may cause a cursor on a graphical user interface, or electronic wheelchair, to move in that direction. When the user changes its intended visual focus to a virtual object in the virtual foreground of a rendered scene, the sensors detect ear-drum complex and/or ear-drum margin and/or other ear structure movement representing convergence of eyes, the effect of which is for the interface to highlight and/or select the virtual object on which the user is focusing their visual attention. The sensor detecting movements of the ear-drum complex and/or ear-drum margin and/or other ear structure on the contralateral (opposite) side may be integrated by the algorithm of the processor to validate the control from the other ear to facilitate eye convergence detection, and/or to alter focal power of variably tunable optics to improve reliability of the interface control, and improve virtual stereoscopic experience of the user by matching vergence and accommodation of the users eyes to the virtual object. The user is, therefore, provided with control of VR and AR virtual scenes, other interface control, movement of a wheelchair, or control of other device(s) by direction of eye movements, and depth of intended focus. By way of example, this could include graded or variable control of the tunable optics, binary control switching between a specified far distance focus optical power (configured for the user's visual acuity, if required) and a near-distance focus optical power. In an AR interface, the optics of the headset corrects for far distance optical errors when the user is focusing on external real rather than virtual objects, and for near-distance correction of presbyopia when focusing on external real objects, and/or in addition to focusing on virtual objects. The optics could be configured for an individual user so the variable far-distance and near-distance optics are appropriate to correct for the optical characteristics of the user's eye-sight in each eye individually.

Detecting ear-drum complex and/or ear-drum margin and/or other ear structure changes owing to eye convergence may alter the virtual rendered scene to move the mid-point of attention to directly in-front of the user, with near-focus optics. This enables the user to look at a virtual interface screen or object of interest that may be peripheral in the virtual scene, to focus on it, and the act of focusing on the area (detected by the sensor owing to convergence of the eyes), brings the virtual image or object into centre of gaze by "virtually dragging" the salient virtual object centrally.

If the user, when looking at any area of the rendered image, focuses its vision on a virtual object that is in "near position" within the virtual scene, the invention detects the two dimension position of the area of visual focus, and provides near visual focus or selection of the area of the virtual scene or virtual object of interest. Tunable optics include the use of any configuration of tunable optics which may include, but not limited to: tunable optic devices sited between the user and the near-eye display (such as a tunable lens or other tunable device), or sited between the near-eye display and the image source, or any other configuration enabling alteration of the users accommodation for the virtual image to match the accommodation expected to accompany the vergence angle of the eyes.

A skilled user imagining one is attending to sound positioned away from the midline, to one side of the head, will result in the sensor detecting the movement of the ear-drum complex and/or ear-drum margin and/or other ear structures, and will cause control of an interface. For example, this could be a cursor on a graphical user interface, or electronic wheelchair or other moveable device, to move in that direction. The data from the sensor detecting movements of the ear-drum complex and/or ear-drum margin and/or other ear structure on the contralateral side may be integrated by the algorithm of the processor to validate the control from the other ear to improve reliability of the interface control. The user is therefore provided with cursor or three-dimensional virtual icon control, other interface control, movement of a wheelchair, control of other device by imagined or real auditory attention to one side. Intentional change in visual or auditory focus provides an additional control, for example, to include a binary control function (such as stopping a wheelchair when converging eyes to look at a near object mounted on a wheelchair, such as a sign exhibiting "Stop/Go" text), or graded control in relation to the distance of intended eye focus and subsequent convergence (such as increased wheelchair speed with distance focus and reduced wheelchair speed with near-focus). Graded control includes moving a robotic or other moving device forward and backwards relative to the user according to the intended visual focus of the user.

The desired function, such as movement control of a robotic prosthetic limb or assistive robotic arm in relation to eye movement, may be activated by a control signal, such as two short duration ear-drum complex movements in rapid succession. This prevents eye-movement or auditory attention during normal activity from triggering a change in the interface or connected device, such as movement of the prosthesis when it is not intentionally desired by the user.

An example of one similar embodiment is the control of a robotic prosthetic arm and hand. One intentional short duration bilateral ear-drum complex movement (subsequently referred to as an "ear-click") changes the state to activate the interface to move the robotic device according to further inputs. Two ear-clicks change the interface to control an extension function at the shoulder and elbow robotic prosthetic joints. With the prosthetic limb in a flexed state at the shoulder and elbow joint, the user focuses its gaze on the prosthetic hand. The user then performs two consecutive ear-clicks to commence an algorithm within the processor of the invention, and the user changes its gaze focus to an object for example, an apple on a table in front of it. The sensors detect the effect of change in convergence of the eyes, causing the shoulder and elbow joints to extend such that the prosthetic arm moves towards the apple. The extension movement stops when the hand of the prosthesis approaches a distance from the user that is configured for the user to represent the distance of eye visual focus. The user performing three ear-clicks changes the status of the prosthetic hand control, and effects an opening of the robotic hand. Ear-drum complex and/or margin and/or other ear structure movements, correlated with vertical eye-movements, are configured so that when the user looks down the prosthetic shoulder joint moves the arm down (flexes the shoulder joint) to a degree to enable the prosthetic hand to contact the apple corresponding to the site of visual focus. The user performing one longer ear click closes the prosthetic hand around the apple. This could further include haptic feedback presented as varying degrees of vibration being communicated to the user by a haptic actuator in the earphone, with the degree of vibration being relative to other input, including, but not limited to, pressure sensors in the fingers of the prosthetic hand. The user is informed to stop the contraction of the prosthetic hand around the apple when the haptic feedback is considered by the user to represent suitable force to grip the apple but not to damage it, by the user generating a further longer ear-click to stop any further movement of the prosthetic. This example is one of many potential control embodiments envisaged.

Additional embodiments similar to that described in the above paragraph above include the robotic hand, or any other robotic feature or mechanism, being physically associated with any range or distance detection sensor (for example a time of flight sensor, LIDAR, or a laser-based or other proximity device or sensor), or any other distance and/or position sensitive sensor and/or associated algorithm, for example imaging sensor and image detection and/or recognition and/or tracking algorithm. Any movement and/or control signal generated by inputs to the processor of the algorithm of the current invention, from the earphone sensor or any other sensor, effects a movement of the robotic arm to move the robotic hand to a specified distance from and close to the sensed object. Therefore, this initiates a control that causes the movement of the robotic device or other device towards the object, and the distance of the movement towards the object is controlled by the data from the range or distance detection, or other similar sensor within the robotic or similar device.

Three-dimensional detection and location methods, for example LIDAR or other three-dimensional imaging sensors or combination of sensors, detecting the location of an object are envisaged. The user selects the object by focusing upon it, and the eye-gaze and eye convergence detected by the sensor triggers the robotic arm to move the robotic hand to a position close to the sensed object, which is controlled by the three-dimensional data. Once positioned, the robotic hand is configured such that further control signal effects movement of the robotic fingers and/or thumb to come into contact with the object, enabling grasp of the object by the robotic hand, and subsequent controlled robotic arm movements to lift the object.

Additional controls of interfaces are envisaged, for example, to include the user focusing vision at a nearer point, such as a target label on a prosthetic arm, and the subsequent change of eye focus and resultant change in eye convergence, and subsequent change in ear-drum complex and/or ear-drum margin and/or other ear structure movements, to effect a change in control of the interface. This may be binary control, for example, an on/off control. A dynamic or moving target, provides a further control option, for example a target may move towards the user when fixated on by eye-gaze, enabling the user to dynamically control an interface, and, when the user visually fixes or focuses away from the target, any further change in the dynamic control is prevented.

In other embodiments, to include spectacles or VR or AR or other headsets or near-eye interfaces, the output from the sensors, associated with user eye focus on a near-object, triggers a sensor such as LIDAR or time of flight or other measurement or proximity device located on the headset or spectacles to provide data input to a processor reflecting the distance between the headset and the object in direct visual line of sight according to eye position. The same or a further trigger might effect a robotic arm to move and position the robotic hand to a specified distance from, and close to, the sensed object. This positions the robotic hand at a location whereby any configured further control signal effects movement of the robotic hand such that the robotic fingers and/or thumb come into contact with the object, enabling grasp of the object by the robotic hand, and subsequent controlled robotic arm movements to lift the object.

Further embodiments include AR or VR devices, or other headsets or near-eye interfaces, where a rendered or virtual or stereoscopic representation of a three-dimensional scene is represented on the graphical user interface with optical adjustment that is configured so that the range of relative degrees of near focus, related to convergence of the eyes, is associated with the full or partial depth of field of the virtual representation. The scene may include a virtual scene or the real scene directly in front of the user, and potentially visible through an AR headset, or a transmitted real scene from another viewpoint or another location. Visual focus (associated with eye convergence) of a point of selection at any virtual three-dimensional coordinate within the scene. This effects control of any interface, such as local or remote robotic arm or virtual selection mechanism, or any other similar interface, to move physically or virtually to any point that coincides with the real-world location or virtual location represented within the position of three-dimensional eye focus in the virtual scene.

Sensors located in spectacles or VR, AR, or other headsets or near-eye interfaces, and the output from those sensors associated with the user changing its visual focus or eye movement (for example a change to central visual focus) or other configured movement or sensor output, effects a movement of a robotic arm or other mechanical or virtual device to move to and perform an action at a predetermined position relative to the device, for example to pick up an object from a conveyor belt of a manufacturing process and move it to another position.

The processor generates an output dependent on the algorithm detecting a movement or change of the ear-drum complex, and/or ear-drum margin and/or other ear-structures. The algorithm is configurable and programmable on an individual basis according to the specific sensor, application, interface and user, to determine the output of the processor dependent on the side and degree, quality, position, area and/or duration and/or combination of movement or movements and/or other changes. The output is communicated to an attached device to trigger a change in the state of the attached device.

These attached devices include graphical user interfaces, to include those on a computer or smart-phone screen, AR or VR devices, near-eye displays, and any other user interfaces. The side or sides of the ear-drum complex and/or ear-drum margin and/or other ear structure movement or movements, or other changes, and/or the direction, amplitude and duration, may cause a graphical cursor or icon on a graphical user interface to move in virtual three-dimensions in relation to these movements, in a similar manner to which eye-tracking interfaces can control movement of a cursor. Functions that may be activated may include, but are not limited to: controlling a graphical cursor or virtual three-dimensional graphical control; highlighting or selection functions; controlling mobility aids, including electric wheelchairs and other vehicles and mobile devices; controlling assistive and non-assistive robotic devices, including prostheses and industrial and consumer robotic devices; and/or interfaces controlling variable or graded controls and/or outputs, including variable visual focus in VR/AR interfaces and spectacles. These attached devices also include devices that record ear-drum complex and/or ear-drum margin and/or other ear structure movement as a biometric or behavioural measure.

A further advantage over existing controls or sensors, is that the location of the sensor wholly or partially in the ear canal fixes the position of the sensor relative to the ear drum position. With involuntary or voluntary head or neck movements, the relative position of the sensor to the ear-drum position does not change and, so, the sensor reliably detects movement of the ear-drum complex and ear-drum margin and other ear structures irrespective of background head or neck movements. This allows accurate sensing of the triggering ear-drum complex and ear-drum margin and other ear structure movements and changes for users who are unable to control head movements, or have involuntary movements, and also when other movements can complicate the detection of trigger movements, such as in vehicles and during other motion. The sensor is operated hands-free and, so, does not rely on users having control of their limbs, or interrupting other activities, such as operating machinery or vehicles. The movement of the ear-drum complex and/or ear-drum margin has been shown by visual imaging and tracking not to be affected by speech, swallowing, chewing, jaw movements or head movements. Advantageously, the invention provides isolated control that is unlikely to be incorrectly triggered by speech, chewing and other normal daily activities and movement.

In a further example, the invention provides control of surgical lasers to focus and target the laser on a specific area of localised tissue, before activating the therapeutic laser, for example during laser eye-surgery, or to control laser cautery during laparoscopic surgery, with or without the benefit of AR visualisation of the surgical field. Other embodiments include the output from the sensor or processor being integrated, within the algorithm, with output from other sensors such as eye movement detection sensors, EMG, EEG, range or distance detection (including time of flight) detectors, or accelerometers detecting head movement, or any biometric change, or any other sensors detecting change in movement of the pinna or any other components of the middle or external ear, which are combined to effect a change in the user interface. This allows several modalities or locations of sensors to improve accuracy of control, including, but not limited to moving a graphical cursor of an interface with the position of eye gaze, and include incorporating vertical movement of a graphical cursor by accelerometers affected by head movements.

In other examples, silent and invisible control of mobile phones, communication devices, home management devices and entertainment devices, and any other device or processor applications that can be triggered by a user interface, through short-range wireless means, such as Bluetooth® or other links from the sensor or its processor to these devices are provided. The sensor can be used and worn like a hearing aid or earphone, or other earphone device, in or adjacent to the ear canal, and can be incorporated into other existing technologies such as hearing aids, earphones, and multi-function ear devices which may include a plurality of functions including, telephone and entertainment audio play back, microphone for telephone, voice communication and voice commands, accelerometers, pulse oximetry, temperature sensors and any other sensors (often termed smart "hearable" devices). This provides a means of silent and invisible and variable/dynamic control of these and other user interfaces.

In an example incorporating a microphone in the earphone containing the sensor, this provides the processor an additional sensor input. The algorithm of the processor is configurable to exclude movement of the ear structures in response to external noises from triggering an output signal by excluding eardrum complex or ear-drum margin or other ear structure movements or changes, from generating an output when these are simultaneous with external noise of defined quality or volume detected by the microphone.

By incorporation the sensor in hearing aids this enables control of relative directional amplification in bilateral hearing aids in response to ear-drum complex and/or ear-drum margin and/or other ear-structure related movements or changes, in response to auditory focus. This provides additional functionality and reliability because the input of data on ear-drum margin movement to the processor, in addition to input of data on ear-drum complex movement, provides additional information that enables the algorithm to validate that the detected movement is linked to change in directional auditory attention-preventing false triggering of interfaces by other movements.

The advantage over the previously mentioned prior art for control of robotics and similar mechanical devices, for commercial, industrial, assistive or leisure or other use includes that it provides control for assistive transport devices for those people whose disabilities hamper control owing to loss or reduction of muscle function. Further, it provides graded or variable, and three-dimensional control of robotic prostheses, and, for other uses, it provides hands-free control enabling concurrent use of other devices or tools or hand activities whilst controlling the interface silently and hands-free (and invisibly in the embodiment encompassing control linked to selective auditory attention).

The invention provides control of interfaces by detection of ear-drum complex, and/or ear-drum margin, and/or other ear structure movements as switch or graded control for interfaces. Binary, for example on/off controls, may also include graded controls dependent on the degree and duration of movement detected by the sensors. Movements and changes of different areas of the ear-drum complex, and ear-drum margin, and other ear structures, and/or changes in ear-canal pressures, may be configured to control different interfaces or interface functions. This has a particular benefit for those users who have impaired motor ability for example those users with locked-in-syndrome who only retain vertical eye movement and upper eyelid movement, but also may retain voluntary tensor tympani (middle ear muscle) control. This is because the cranial nerves and structures controlling these movements are located high in the brainstem, above the area of damage that prevents other motor movement. The present invention provides a method and device for detecting vertical eye movement to control assistive and augmentative devices and methods, and any other interface and/or function for any user with or without motor function impairments. Specific defined character and/or combinations of ear-drum complex, and/or ear-drum margin, and/or other ear structure movements are associated with vertical eye movement, providing a means of communicating and control for users with locked-in-syndrome, and for any users with or without motor function impairments, which is likely to be more widely controllable by a greater number of users.

The present invention provides improved function of VR/AR and other graphical, and near-eye interface devices and their control by user intention, by incorporating an alternative to eye-tracking detected by sensors in earphones. Further, improved function in: determining central focus and near-vision focus; in controlling other interfaces in a three-dimensional manner; correcting presbyopia in spectacles and other devices; providing widely applicable assistive and augmentative communication interfaces for users with severe motor impairments, is provided.

The addition of information from ear-drum margin and other ear structure movements to information on ear-drum complex movements, provides improved control beyond that of prior art, by detecting gaze focusing movements, enabling central control of virtual cursors and virtual object selection, and also three-dimensional control and change in such interfaces.

Advantageously, the invention provides a previously undescribed apparatus and method for more reliable control of interfaces and devices from earphones, providing hands-free, silent, three-dimensional and directional control related to two dimensional eye-movements in addition to visual focus, and directional auditory focus.

In a third embodiment, FIGS. 14 to 16—in addition to the subject-matter of FIGS. 1 to 4—discloses a sensor worn by a user in or adjacent the ear canal 2, with the sensor detecting ear-drum complex 5*a* and/or ear-drum 3 margin and/or other ear structure movements or changes, which generates an output to control an interface dependent on changes detected. In particular, detected eye-brow raising or firm eye-lid closure is detected though corresponding movements of the ear-drum complex and/or ear-drum margin and/or other ear structure movements or changes.

FIG. 14 is a graphical representation showing measurement of movements of the ear-drum complex 5*a* and the margin of the ear-drum 3 detected by sensor 1 being a video camera with associated LED light source within the ear-phone 6. The camera within the sensor 1 may use any fixed point, or area, on the ear-drum complex 5*a* and/or ear-drum 3 margin to record movement 12; 13 thereof and, for example, may record a position of the lower end of the malleus 4 and/or any section or length of the ear-drum 3 margin. The position and movement of any of these struc-tures is detected by the video camera sensor 1 and the position is represented as two lines 732; 736 on the graph 729, where the y axis 730 represents the position and measurement of movement, and the x axis 731 represents time. Movements 12; 13 of the ear-drum complex 5*a* are represented on the graph as line 736, and movements of a lower posterior section of the ear-drum 3 margin are repre-sented on the graph as line 732. Movement concurrent with eye-brow 737 elevation 738 is detected by the sensor 1, by detecting movement 12; 13 of the malleus 4 and the change of position (movement 12; 13) of the malleus 4 and the ear-drum 3 (ear drum complex 5*a*) including in a vertical direction, and by also detecting concurrent movement of the section of ear-drum 3 margin. This change of position of the malleus 4 detected by the sensor 1 is shown as a deflection of the line 736, and the change in position of the ear-drum 3 margin is shown as a deflection of the line 732. As the eye-brow 737 elevates 738, the sensor 1 detects movement of the ear-drum complex 5*a* and of the ear-drum 3 margin. As the movements are detected, a signal is output from the sensor 1 to the processor and its algorithm. The output of the processor is dependent upon a comparison between ear-drum complex 5*a* movement and ear-drum 3 margin move-ment and effects a change in a user interface 739, for example to select an alphanumeric key 742 which is corre-spondingly highlighted on a scanning virtual on-screen keyboard 740. In this example, an upwards movement of the ear-drum complex 5*a* in the proximity of the malleus 4, associated with a much lower amplitude or no movement of the ear-drum 3 margin, occurs concurrently with eye-brow 737 elevation 738. The output of algorithm of the processor effects a change in the interface 739 that is configured to be controlled by elevating 738 the eye-brow(s) 737. The user interface 739 is a virtual display of a keyboard 740 on a graphical interface screen 739, which highlights rows of the keyboard 740 sequentially, and subsequently highlights groups of keys and individual keys sequentially 742. The output from the processor effects a selection control and may generate an output of the key 741 that is highlighted graphi-cally 742 at the time the output of the processor is generated. For example, eye-brow 737 raise 738 provides control of a virtual keyboard 740 employed to enable a user with neuro-disabilities to communicate.

FIG. 15 is a graphical representation showing measure-ment of movements of the ear-drum complex 5*a* and the margin of the ear-drum 3 detected by sensor 1 being a video camera with associated LED light source within the ear-phone 6. The camera within the sensor 1 may use any fixed point, or area, on the ear-drum complex 5*a* and/or ear-drum 3 margin to record movement 12; 13 and, for example, may record position of the lower end of the malleus 4 and/or any section or length of the ear-drum 3 margin. The position and movement of any of these structures is detected by the video camera sensor 1 and the position is represented as two lines 732; 736 on the graph 729, where the y axis 730 represents the position and measurement of movement, and the x axis 731 represents time. Movements 12; 13 of the ear-drum complex 5*a* are represented on the graph as line 736, and movements of a lower anterior (front) section of the eardrum 3 margin are represented on the graph as line 732. Firm eye-lid 743 closure 744 is detected by the sensor 1, by detecting movements 12; 13 of the malleus 4 and the change of position (movement 12; 13) of the malleus 4 and the ear-drum 3 (ear drum complex 5*a*), and by also detecting movement of the lower anterior section of ear-drum 3 margin. This change of position of the malleus 4 detected by the sensor 1 is shown as a deflection of the line 736, and the change in position of the ear-drum 3 margin is shown as a deflection of the line 732. As the eye-lid 743 firmly closes 744, the sensor 1 detects movement of the ear-drum complex 5*a* and of the ear-drum 3 margin. As the movements are detected, a signal is output from the sensor 1 to the processor and its algorithm. The output of the processor is dependent upon a comparison between ear-drum complex 5*a* move-ment and ear-drum 3 margin movement and effects a change in a user interface 739, for example to select an alphanu-meric key 742 which is concurrently highlighted 742 on a scanning virtual on-screen keyboard 740. A forward (ante-rior) movement of the ear-drum complex 5*a* in the proximity of the malleus 4, associated with a much lower amplitude or no movement of the ear-drum 3 margin, occurs currently with firm eye-lid 743 closure 744 of the eye-lid 743 on the same side of the face as the sensor 1. The output of the algorithm of the processor effects a change in an interface 739 configured to be controlled by firm eye-lid 743 closure 744. The user interface 739 is a virtual display of a keyboard 740 on a graphical interface screen 739, which highlights rows of the keyboard 740 sequentially, and subsequently highlights groups of keys and individual keys 742 sequen-tially. The output from the processor effects a selection control, and may generate an output of the key 741 that is highlighted graphically 742 at the time the output of the processor is generated. By way of example, firm eye-lid 743 closure 744 provides control of virtual keyboards 740 employed to enable a user with neuro-disabilities to com-municate.

FIG. 16 is a flowchart showing a process for detecting ear movements and output to a processor in the earphone 6 by wired or wireless communication 716. The sensor 1 detects the position, amplitude/degree, direction and/or other char-acteristic of the ear-drum complex 5*a* and ear-drum 3 margin movement, and the output signal, incorporating information on the position amplitude/degree and/or direction of move-ments and/or other characteristic of the ear-drum complex 5*a* and ear-drum 3 margin, is transmitted to the processor of the earphone 6 by wired or wireless communication 717. The algorithm of the processor effects a change in a user interface when the output is generated by the sensor 1 detecting movements of the ear-drum complex 5*a* and/or ear-drum 3 margin that correspond to eye-brow 737 raising 738 by the user 722. On receiving input from the sensor 1 that is generated in association with the user raising 738 its eye-brows 737, the apparatus is configured to control the output to select 741 a highlighted graphical (or virtual) key 742 on a graphical representation of a keyboard (an 'on-screen keyboard') 740 on a computer graphical interface (screen) 739. This provides a means for communication for the user of the earphone by generating text 741 on a computer or other graphical interface 739; 723.

The movement is also of greater amplitude than looking up without significant eye-brow elevation (as occurs with sub-maximal vertical gaze), or associated with reflex or gentle blinking (upper lid closure) effected by palpebral obicularis muscle (during "normal" eye-closing).

Advantageously, the invention provides the ability to effect single modality control, such as a binary on/off interface by eye-brow raising or lowering, or firm eye-lid closing or opening. Alternatively, the invention provides dual control, which may have different actions on the same, or different, interfaces dependent upon either eye-brow movement or eyelid movement. As the patterns and combinations of movements of the ear-drum complexes, ear-drum margin and/or other ear structures are different from that shown with tensor tympani reflex and voluntary control, and with eye-movements, the invention provides additional controls which can interface either in conjunction or separately from those other controls. Graded movement of the eye-brows and eye-closure also provides graded and/or variable control of interfaces. Individual (unilateral, or one-sided) eye-lid control, and in some people individual eye-brow control, provides further control of interfaces. For example, left eye-lid closure could affect one function of an interface or one interface, and right eye-lid closure could affect another function of the interface or another interface.

When the earphone has a voluntary ear-drum control switch functionality in combination with the above, this provides a further level of control from ear-drum complex and/or ear-drum margin and/or associated ear structure movement or change. The combination enables the user to have multi-functional control of interfaces. For example, this could be three separate switch controls by: 1) voluntary tensor tympani contraction; 2) eye-brow raising; and 3) firm eye-lid closure. Alternatively, those three controls could be utilised to provide further degrees of variable control of interfaces affected by graded movements of the controlling muscles.

The present invention provides a method and device for detecting eye-lid and/or other preserved facial movement to control assistive and augmentative devices and methods, and any other interface and/or function for any user with or without motor function impairments. The use of eye-brow raise does not require the user to move its focus of gaze. The current invention therefore provides a control but avoids interruption of user's activity—for example reading text or eye-tracking interfaces that occurs with vertical eye movement. An advantage over previously described interfaces is that eye-brow raising and firm eye-closure are widespread abilities in healthy users and so will not need to be learnt; whereas, interfaces controlled by voluntary ear-drum movement are limited by the proportion of people who have voluntary control, or can be trained to develop voluntary control.

This present invention provides a previously undescribed method and apparatus for more widespread control of interfaces and devices from earphones, providing hands-free and silent control for a larger proportion of users, without intensive training and including the ability to monitor other head and neck muscle movements.

In a fourth embodiment, the invention of FIGS. 17 to 20—in addition to the subject-matter of FIGS. 1 to 4—provides an apparatus and method for controlling hearing-aids, hearing assistive devices, or hearables to amplify the frequencies and sounds of interest by detecting the ear-drum complex movements that are associated with intended selective auditory attention.

FIG. 17 is a flowchart showing the sensor 1 being within an earphone 6, and the sensor 1 detects movement 416 of the ear drum complex 5a. The output of the sensor 1 in response to movement 12; 13 of the ear-drum complex 5a and/or ear-drum 3 margin (or another discernible change) is transmitted to the processor within the earphone 6; as per 417. The algorithm 418 of the processor effects a change in the transmitted sound output from the earphone 6 determined by the algorithm which incorporates data from movement of the ear-drum complex. When the sensor 1 detects that the ear-drum 3 moves away from the sensor, the algorithm increases the amplitude of sound output corresponding to usual speech frequencies 419 from the earphone 6. If the user is wearing a similar device in each ear, the sensor 1 in the earphone 6 in the opposite ear may detect movement of the adjacent ear-drum towards the sensor, and the algorithm of the earphone 6 reduces the amplitude of sound output 420. The resultant effect is to selectively increase the sound amplitude of usual speech frequencies in one hearing aid, and reduce the sound amplitude output of the hearing aid of the opposite ear, enabling the user to better hear speech to one side of the head to which he/she has selective attention.

FIG. 18 is a flowchart showing sensors within earphones 6, one in each ear. The outputs from the sensors 1 and/or processor in each of the two earphones worn by the user are communicated to the processor of the device worn in the opposite ear of the user by wired or wireless communication method 421. The algorithm detects the difference between the movement of each ear-drum complex of the user towards or away from the respective sensor, and controls the relative amplitude and frequencies output 422 from the attached earphone 6 following directional selective auditory attention. Thereby, selectively improving the sound output in the earphone(s) according to the direction of attention 423.

FIG. 19 is a flowchart showing a process of detecting ear-drum complex movement and output to a processor in the earphone 6, as per 416; 417; 418. The sensor 1 detects the amplitude, direction and frequency of vibration of the ear-drum movement, and the output signal incorporates information on the degree and direction of movement of the ear-drum complex, and is transmitted to the processor of the earphone 6. The algorithm controls the amplitude of specific frequencies of sound output from the earphone 6 dependent upon the amplitude and direction of movement of the detected ear-drum 424. In this example, the earphone amplifies and outputs frequencies of sound that the user is attempting to selectively attend to 425.

FIG. 20 is a flowchart showing the sensor 1 within an earphone 6, and the sensor 1 detects movement 416 of the ear drum complex 5a. The earphone emits a sound, tone or series of tones (subsequently referred to as 'test sound') 426. The sensor 1 detects movement 416 of the ear drum complex 5a (including frequency of vibration) in response to the emitted test sound or tone, which may be a single measurement, or a multitude of measurements in order to provide an output. The output of the sensor, in response to the movement, is transmitted 417 to a processor within the earphone. In this example, the algorithm of the processor 427 processes data from movement of the ear-drum complex 5, and effects a change in the profile of amplification and/or transmission of specific frequencies of transmitted sound output from the device. The resultant effect is to program the device to selectively increase the amplitude of sound output of any specific frequencies that had resulted in lower than an expected threshold of movement/vibration and/or resonance of the ear-drum complex 5a to those frequencies when emitted as the test sound. This enables the user to hear better as the sound output from the earphone to the user's ear is tailored to the user's specific hearing deficiencies 428.

No known prior art discloses control of user interfaces by detecting ear-drum complex movement as a surrogate for detection of eye-movement per se, or using intentional change in auditory focus to control a user interface other than hearing aid amplitude or frequency.

For selective auditory attention a user attending to sound positioned away from the midline, to one side of the head, the sensor detects movement of the ear-drum complex on the ipsilateral side, which may cause the amplitude of the sound emitted from the ipsilateral hearing aid or assistive hearing or hearable device to increase. The sensor detecting movement of the ear-drum complex on the contralateral side may cause the amplitude of sound emitted from the contralateral hearing aid or assistive-hearing device or hearable device to decrease. The user is therefore provided with increased amplification of frequencies of interest (for example speech sound frequencies) on the side of auditory attention, improving hearing function.

In another example, output from sensors from two hearing aids, assistive hearing or hearable devices both provide input data to the algorithm of the processor. This would enable the processor and its algorithm to change the quality and type of the emitted sound in relation to a detected difference between movements of the ear-drum complexes on each side. This would enhance the reliability of control of selective auditory attention by producing more validated control based on confirmation of the reciprocal movement of the ear-drum complex.

In a further embodiment, in addition to output from sensors from one or two hearing aids or assistive hearing or hearable devices, a device such as a remote microphone, including a microphone in a mobile phone, watch or any other device, may provide additional input data to the algorithm of the processor. This would also enable information from ambient sound to enable further triangulation of the sound of intended auditory attention by referencing the movement of the ear-drums to information from the remote microphone, and enable further amplification and transmission of the sound of intended auditory attention to the ear of the user.

The output from the contralateral sensors and the remote microphones may be transmitted by wire or wireless communication to the hearing aid, hearing assistive or hearable device, and to other devices such as mobile phones and watches.

Algorithms for control of the sound output may be located within processors within the hearing aid, hearing assistive or hearable device, and/or within mobile phones or other wired or wirelessly connected devices.

Those skilled in the art will know that some detectors require an appropriate emitter in order to detect a change or movement. Accordingly, such emitters may include visible light, non-visible light (including infra-red) through light emitting diodes, laser, etc., ultrasound, and/or other emitters. This list is non-exhaustive.

Those skilled in the art will understand and know that various attributes or advantages disclosed in relation to a single embodiment may well be equally applicable attributes or advantages of one or more of the other embodiments.

The invention claimed is:

1. A wearable apparatus for detecting either movements or changes in an ear structure of a user in order to control or affect a function of an associated device, wherein the wearable apparatus comprises:

a sensor apparatus that is configured to be worn by said user to be located in an ear-canal of said user, the sensor apparatus including at least one sensor being wholly or partially located in said ear-canal to have a position of the sensor fixed relative to a position of an ear-drum of said user such that the sensor apparatus detects either movements or changes of characteristics of a middle ear, an ear-drum complex, an ear-drum margin, and/or associated ear structures without detecting ear movements caused by jaw movements, and the sensor apparatus being configured to capture sensor data relating to the movements or the changes of characteristics; and a processor for processing and analysing the sensor data from the sensor apparatus, wherein the processor is configured to:

determine eye movement or directional auditory attention or focus by analysing the sensor data relating further to a degree, speed, size of movement or change, or duration of movement of the middle-ear, the ear-drum complex, the ear-drum margin, and/or the associated ear structures, as isolated from ear movements caused by jaw movements such that, through identification of change(s) or difference(s) in the sensor data, the wearable apparatus is capable of controlling or affecting the function of the associated device.

2. The wearable apparatus as claimed in claim 1, wherein the sensor apparatus is configured to detect change in:

(a) movement of the ear-drum complex, or the associated ear structures, through two or three dimensional analysis or image processing;

(b) distance from the sensor apparatus;

(c) direction of movement, size of movement, degree of movement, duration of movement, position, and/or shape of a part or whole of the ear-drum complex, an auditory canal, the ear-drum margin, an adjacent wall of an auditory tube and/or the associated ear structures;

(d) colour of at least part of the ear-drum complex or the associated ear structures;

(e) frequency of vibration of at least part of the ear-drum complex;

(f) reflection;

(g) any other measure indicating movement of the ear-drum complex and/or the associated ear structures; and/or (h) any one or more of (a) to (g) providing a discernible difference between different areas of the ear structure or different ear structures, or a pair of sensors, each associated with a different ear of the user.

3. The wearable apparatus as claimed in claim 1, wherein the sensor apparatus further comprises:

an imaging detector;

a thermal imaging detector;

a static or scanning laser detector;

a time of flight detector;

LIDAR (laser imaging, detection, and ranging);

laser triangulation;

laser Doppler vibrometry;

digital holography;

optical coherence tomography;

a photoplethysmograph (PPG) sensor, with or without an oxygen saturation sensor;

and/or an ultrasonic detector.

4. The wearable apparatus as claimed in claim 1, wherein controlling or affecting the function of the associated device comprises:

(i) operating as an intentional switch trigger;

(ii) graduated or variable intentional control;

(iii) two or more dimensional or variable control of user interfaces;

(iv) controlling direction, amplitude and frequency of sound output of earphone device;

(v) optical focus control;

(vi) multi-functional control of a same interface or different interfaces;

change in state of a device;

(vii) control of a digital, electronic of other device, or electronic interface, including those remote from said user;

(viii) virtual or real movement control; and/or (ix) monitoring movements of the ear-drum complex, the ear-drum margin or the associated ear structures as a biometric measure of health, disease, physiological and behavioural activity.

5. The wearable apparatus as claimed in claim 1, wherein, processing and analysing the sensor data provides:

(i) graduated, dynamic or variable control of interfaces by detecting movements of the ear-drum complex, the ear-drum margin and/or the associated ear structures; and/or (ii) intentional graduated, dynamic or variable control of the interfaces by detecting voluntary movements of the ear-drum complex, the ear-drum margin and/or the associated ear structures.

6. The wearable apparatus as claimed in claim 1, wherein, the wearable apparatus comprises a further sensor apparatus that is configured to be worn by said user to be located in or adjacent a second ear-canal of said user to provide additional sensor data.

7. The wearable apparatus as claimed in claim 6, wherein, the processor is configured to receive the sensor data from the sensor apparatus and the further sensor apparatus and is configured to utilize identified change(s) or difference(s) in two sets of the sensor data to control or affect the function of the associated device.

8. The wearable apparatus as claimed in claim 1 further comprising a feedback apparatus.

9. The wearable apparatus as claimed in claim 1 further comprising an apparatus for detecting eye-convergence, gaze focusing, depth of intended visual focus, horizontal and/or vertical eye movements, or any combination thereof.

10. The wearable apparatus as claimed in claim 1, wherein the processor is configured to determine eye movement or directional auditory attention or focus by analysing the sensor data relating further to the degree of movement of the middle-ear, the ear-drum complex, the ear-drum margin, and/or the associated ear structures.

11. The wearable apparatus as claimed in claim 1, wherein the processor is configured to determine eye movement or directional auditory attention or focus by analysing the sensor data relating further to the speed of movement of the middle-ear, the ear-drum complex, the ear-drum margin, and/or the associated ear structures.

12. The wearable apparatus as claimed in claim 1, wherein the processor is configured to determine eye movement or directional auditory attention or focus by analysing the sensor data relating further to the size or change of movement of the middle-ear, the ear-drum complex, the ear-drum margin, and/or the associated ear structures.

13. The wearable apparatus as claimed in claim 1, wherein the processor is configured to determine eye movement or directional auditory attention or focus by analysing the sensor data relating further to the duration of movement of the middle-ear, the ear-drum complex, the ear-drum margin, and/or the associated ear structures.

14. A method for detecting either movements or changes in an ear structure of a user in order to control or affect a function of an associated device, wherein the method comprises:

detecting and capturing sensor data from a sensor apparatus worn by the user and located in an ear-canal of the user, the sensor apparatus including at least one sensor being wholly or partially located in said ear-canal to have a position of the sensor fixed relative to a position of an ear-drum of said user such that the sensor apparatus detects either movements or changes of characteristics of a middle ear, an ear-drum complex, an ear-drum margin, and/or associated ear structures without detecting ear movements caused by jaw movements, and the sensor apparatus being configured to capture the sensor data relating to the movements or the changes of characteristics;

determining eye movement or directional auditory attention or focus, by analysing the sensor data relating further to a degree, speed, size of movement or change, or duration of movement of the middle-ear, the ear-drum complex, the ear-drum margin, and/or the associated ear structures, as isolated from ear movements caused by jaw movements; and utilising identified change(s) or difference(s) in the sensor data to control or affect the function of the associated device.

15. The method as claimed in claim 14, wherein processing and analysing the sensor data comprises detecting change in:

(a) movement of the ear-drum complex, or the associated ear structures, through two or three dimensional analysis or image processing;

(b) distance from the sensor apparatus;

(c) direction of movement, size of movement, degree of movement, duration of movement, position, and/or shape of a part or whole of the ear-drum complex, an auditory canal, the ear-drum margin, an adjacent wall of auditory tube and/or the associated ear structures;

(d) colour of at least part of the ear-drum complex or the associated ear structures;

(e) frequency of vibration of at least part of the ear-drum complex;

(f) reflection;

(g) any other measure indicating movement of the ear-drum complex and/or the associated ear structures; and/or (h) any one or more of (a) to (g) providing a discernible difference between different areas of the ear structure or different ear structures, or a pair of sensors, each associated with a different ear of the user.

16. The method as claimed in claim 14, wherein controlling or affecting the function of the associated device comprises:

(i) operating as an intentional switch trigger;

(ii) graduated or variable intentional control;

(iii) two or more dimensional or variable control of user interfaces;

(iv) controlling direction, amplitude and frequency of sound output of earphone device;

(v) optical focus control;

(vi) multi-functional control of a same interface or different interfaces;

change in state of a device;

(vii) control of a digital, electronic or other device, or electronic interface, including those remote from said user;

(viii) virtual or real movement control; and/or (ix) monitoring movements of the ear-drum complex, the ear-drum margin or the associated ear structures as a biometric measure of health, disease, physiological and behavioural activity.

17. The method as claimed in claim 14 wherein processing and analysing the sensor data concerning eye movement or directional auditory attention/focus data provides:

(i) graduated, dynamic or variable control of interfaces by detecting movements of the ear-drum complex, the ear-drum margin and/or the associated ear structures; and/or (ii) intentional graduated, dynamic or variable control of the interfaces by detecting voluntary movements of the ear-drum complex, the ear-drum margin and/or the associated ear structures.

18. The method as claimed in claim 14 further comprising detecting eye-convergence, gaze focusing, depth of intended visual focus, horizontal and/or vertical eye movements, or any combination thereof.

19. The method as claimed in claim 14 further comprising receiving the sensor data from sensors worn in both ears of said user and utilising identified change(s) or difference(s) in two sets of the sensor data to control or affect the function of an associated device.

20. A wearable apparatus for detecting either movements or changes in an ear structure of a user in order to control or affect a function of an associated device, wherein the wearable apparatus comprises:

a sensor apparatus that is configured to be worn by said user to be located in an ear-canal of said user, the sensor apparatus including at least one sensor being wholly or partially located in said ear-canal to have a position of the sensor fixed relative to a position of an ear-drum of said user such that the sensor apparatus detects either movements or changes of characteristics of a middle ear, an ear-drum complex, an ear-drum margin, and/or associated ear structures without detecting ear movements caused by jaw movements, and the sensor apparatus being configured to capture sensor data relating to the movements or the changes of characteristics; and a processor for processing and analysing the sensor data from the sensor apparatus, wherein the processor is configured to determine vertical eye movement or eye-convergence by analysing the sensor data relating further to a degree, speed, size of movement or change, or duration of movement of the middle-ear, the ear-drum complex, the ear-drum margin, and/or the associated ear structures, as isolated from ear movements caused by jaw movements such that, through identification of change(s) or difference(s) in the sensor data, the wearable apparatus is capable of controlling or affecting the function of the associated device.

21. A wearable apparatus for detecting either movements or changes in an ear structure of a user in order to control or affect a function of an associated device, wherein the wearable apparatus comprises:

a sensor apparatus that is configured to be worn by said user to be located in an ear-canal of said user, the sensor apparatus including at least one sensor being wholly or partially located in said ear-canal to have a position of the sensor fixed relative to a position of an ear-drum of said user such that the sensor apparatus detects either movements or changes of characteristics of a middle ear, an ear-drum complex, an ear-drum margin, and/or associated ear structures without detecting ear movements caused by jaw movements, and the sensor apparatus being configured to capture sensor data relating to the movements or the changes of characteristics; and a processor for processing and analysing the sensor data from the sensor apparatus, wherein the processor is configured to analyze voluntary control data by analysing the sensor data relating further to a degree, speed, size of movement or change, or duration of movement of the middle-ear, the ear-drum complex, the ear-drum margin, and/or the associated ear structures, as isolated from ear movements caused by jaw movements such that, through identification of change(s) or difference(s) in the sensor data, the wearable apparatus is capable of controlling or affecting the function of the associated device.

* * * * *